(12) United States Patent
Hu et al.

(10) Patent No.: US 12,268,740 B2
(45) Date of Patent: Apr. 8, 2025

(54) FILAMENTOUS NANOPARTICLES HAVING VACCINE ADJUVANT EFFECT

(71) Applicant: Croda International Plc, Goole (GB)

(72) Inventors: Kefei Hu, Frederikssund (DK); Laurent Duroux, Frederikssund (DK); Erik Lindblad, Frederikssund (DK)

(73) Assignee: Croda International Plc, East Yorkshire (GB)

( * ) Notice: Subject to any disclaimer, the term of this patent is extended or adjusted under 35 U.S.C. 154(b) by 763 days.

(21) Appl. No.: 17/312,796

(22) PCT Filed: Dec. 16, 2019

(86) PCT No.: PCT/EP2019/085444
§ 371 (c)(1),
(2) Date: Jun. 10, 2021

(87) PCT Pub. No.: WO2020/127115
PCT Pub. Date: Jun. 25, 2020

(65) Prior Publication Data
US 2023/0321227 A1    Oct. 12, 2023

(30) Foreign Application Priority Data

Dec. 18, 2018 (EP) .................................... 18213540

(51) Int. Cl.
*A61K 39/39* (2006.01)
*A61K 9/107* (2006.01)
*A61K 39/00* (2006.01)

(52) U.S. Cl.
CPC ............ *A61K 39/39* (2013.01); *A61K 9/1075* (2013.01); *A61K 2039/55555* (2013.01); *A61K 2039/55577* (2013.01)

(58) Field of Classification Search
CPC .................. A61K 39/39; A61K 9/1075; A61K 2039/55555; A61K 2039/55577
See application file for complete search history.

(56) References Cited

U.S. PATENT DOCUMENTS

| | | | |
|---|---|---|---|
| 2,802,005 | A | 8/1957 | Heidelberger et al. |
| 3,046,301 | A | 7/1962 | Phillips et al. |
| 3,803,124 | A | 4/1974 | Arcamone et al. |
| 4,020,270 | A | 4/1977 | Arcamone et al. |
| 4,046,878 | A | 9/1977 | Patelli et al. |
| 4,307,100 | A | 12/1981 | Langlios et al. |
| 4,377,687 | A | 3/1983 | Eisenbrand |
| 4,814,470 | A | 3/1989 | Colin et al. |
| 4,857,653 | A | 8/1989 | Colin et al. |
| 5,476,954 | A | 12/1995 | Bourzat et al. |
| 5,821,337 | A | 10/1998 | Carter et al. |
| 2007/0212329 | A1 | 9/2007 | Bruck et al. |
| 2008/0069832 | A1 | 3/2008 | Chomez et al. |
| 2014/0234349 | A1 | 8/2014 | Morein et al. |
| 2015/0313991 | A1 | 11/2015 | Ferreira Chiesa et al. |

FOREIGN PATENT DOCUMENTS

| | | | |
|---|---|---|---|
| CN | 1889977 | A | 1/2007 |
| CN | 1956729 | A | 5/2007 |
| CN | 103857403 | A | 6/2014 |
| CN | 105169386 | A | 12/2015 |
| DE | 2124023 | A1 | 12/1971 |
| EP | 0111058 | A1 | 9/1983 |
| EP | 0122707 | A1 | 3/1984 |
| EP | 0137145 | A1 | 7/1984 |
| EP | 0253738 | A1 | 1/1988 |
| EP | 0253739 | A1 | 1/1988 |
| EP | 0321122 | A2 | 11/1988 |
| EP | 0698611 | A1 | 2/1996 |
| EP | 0902015 | A1 | 3/1999 |
| GB | 1235022 | | 7/1971 |
| RU | 2010 115 549 | A | 10/2011 |
| WO | 9209589 | A1 | 6/1992 |
| WO | 9222653 | A1 | 12/1992 |
| WO | 9302094 | A1 | 2/1993 |
| WO | 9404679 | A1 | 3/1994 |
| WO | WO-2013051994 | A1 * | 4/2013 ........... A61K 31/255 |
| WO | 2014163558 | A1 | 10/2014 |

OTHER PUBLICATIONS

S. G. Verza, P. E. de Resende, S. Kaiser, L. Quirici, H. F. Teixeira, G. Gosmann, F. Ferreira2, G. G. Ortega Micellar aggregates of saponins from Chenopodium quinoa: characterization by dynamic light scattering and transmission electron microscopy doi: 10.1691/ph.2012.1102 (Year: 2012).*

Bunyamin Karagoz, Lars Esser, Hien T. Duong, Johan S. Basuki, Cyrille Boyer and Thomas P. Davis Polymerization-Induced Self-Assembly (PISA)—control over the morphology of nanoparticles for drug delivery applications DOI: 10.1039/c3py01306e (Year: 2014).*

S. G. Verza et al.: Micellar aggregates of saponins from Chenopodium quinoa: characterization by dynamic light scattering and transmission electron microscopy; doi: 10.1691/ph.2012.1102 (Year: 2012).*

Bunyamin Karagoz; Polymerization-Induced Self-Assembly (PISA)—control over the morphology of nanoparticles for drug delivery applications DOI: 10.1039/c3py01306e (Year: 2014).*

Demana et al., "A Comparison of Pseudo-Ternary Diagrams of Aqueous Mixtures of Quil A, Cholesterol and Phospholipid Prepared by Lipid-Film Hydration and Dialysis", Journal of Pharmacy and Pharmacology, (May 2004), vol. 56, No. 5, pp. 573-580.

(Continued)

*Primary Examiner* — Robert A Wax
*Assistant Examiner* — Andre Mach
(74) *Attorney, Agent, or Firm* — Buchanan Ingersoll & Rooney PC

(57) ABSTRACT

The present invention relates to filamentous, i.e. thread-like nanoparticles comprising sterol and a component derived from *Quillaja saponaria* Molina selected from quillaja acid and quillaja saponin. More particularly, the invention relates to the use of said thread-like nanoparticles in vaccines and drug delivery or adsorption systems systems, methods for their production and uses thereof, such as for use as a vaccine adjuvant and in cancer therapy.

13 Claims, 17 Drawing Sheets

(56) References Cited

OTHER PUBLICATIONS

Office Action (The First Office Action) issued Jan. 12, 2024, by the State Intellectual Property Office of People's Republic of China in corresponding Chinese Patent Application No. 201980083532.7 and an English translation of the Office Action. (14 pages).

Boyaka et al., "Oral QS-21 Requires Early IL-4 Help for Induction of Mucosal and Systemic Immunity", The Journal of Immunology, 2001, vol. 166; pp. 2282-2290.

Sjölander et al., "ISCOMs: An Adjuvant with Multiple Functions", Journal of Leukocyte Biology, 1998, vol. 64, pp. 713-723.

Oda et al., "Adjuvant and Haemolytic Acivities of 47 Saponins Derived from Medicinal and Food Plants", Biol Chem., 2000, vol. 381, No. 1, pp. 67-74 (abstract ony).

Xie el al. "Platycodin D is a Potent Adjuvant of Specific Cellular Humoral Immune Responses Against Recombinant Hepatitis B Antigen", Vaccine, 2009, vol. 27, Issue 5, pp. 757-764.

De Groot et al., "Novel Colloidal Microstructures of β-Escin and the Liposomal Components Cholesterol and DPPC". Published online May 24, 2018, Planta Med. 2018; 84: 1219-1227, Georg Thieme Verlag KG Stuttgart, New York.

European Search Report for European Application No. EP18213540, dated Jun. 7, 2019, 5 pages.

International Search Report and Written Opinion for International Application PCT/EP2019/085444, dated Feb. 14. 2020, 13 pages.

Lendermans et al., "Immuno-stimulating Complexes Prepared by Ethanol Injection", Journal of Pharmacy and Pharmacology, 2005, 57: 729-733.

Mazeyka et al., "Elaboration of Immune Stimulating Lipid-Saponin Subunit Antigen Carrier Based on Glycolipid Monogalactosyldiacylglycerol from Sea Macrophytes and Triterpene Glycosides from Cucumaria japonica", Biophysics, 2013, vol. 58, No. 5, pp. 616-623.

Verza et al., "Micellar Aggregates of Saponins from Chenopodium quinoa: Characterization by Dynamic Light Scattering and Transmission Electron Microscopy", Pharmazie 67, 2012, 5 pages.

Hinde et al. in "Pair correlation microscopy reveals the role of nanoparticle shape in intracellular transport and site of drug release", Nature Nanotechnology, vol. 12, pp. 81-89 (2017).

Karagoz et al. "Polymerization-Induced Self-Assembly (PISA)—control over the morphology of nanoparticles for drug delivery applications.", Polym. Chem., 2014, pp. 350-355.

Kensil et al., "Separation and characterization of saponins with adjuvant activity from Quillaja saponaria Molina cortex", The Journal of Immunology, 1991, 146(2), 431-437.

Taiwanese Office Action with Search Report for Taiwanese Application No. 108145097, dated May 31, 2023, 10 pages.

* cited by examiner

FIG.5
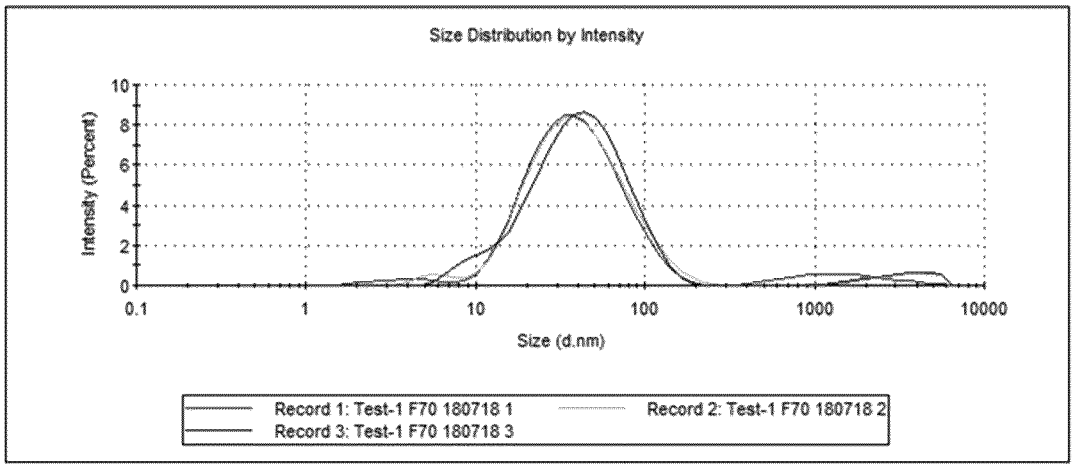
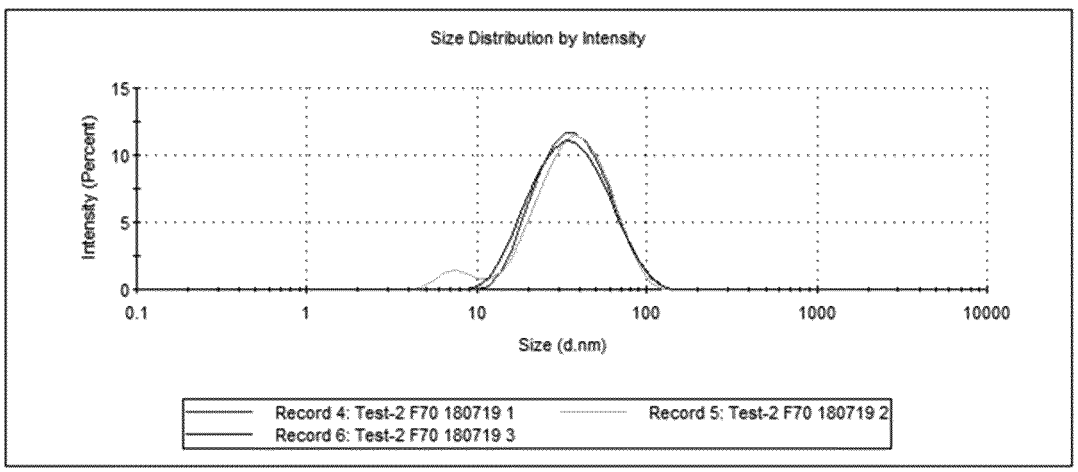
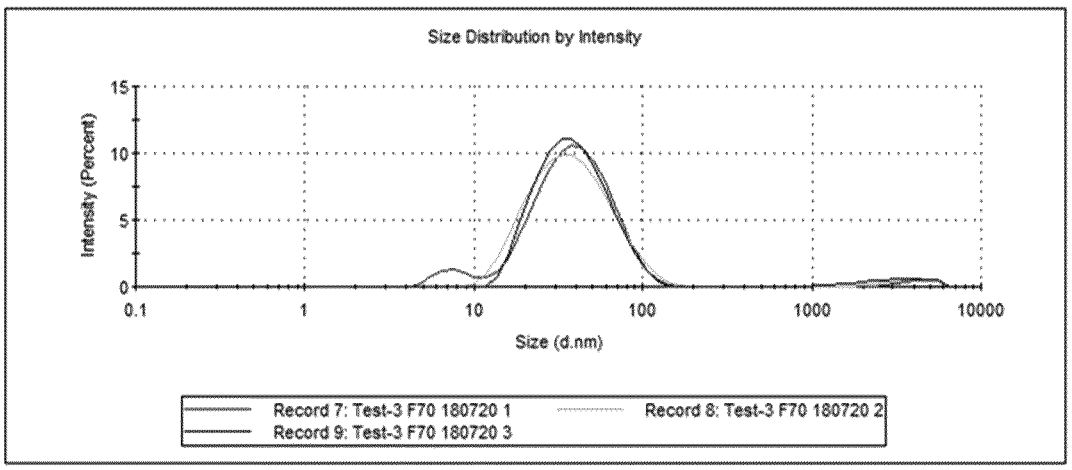

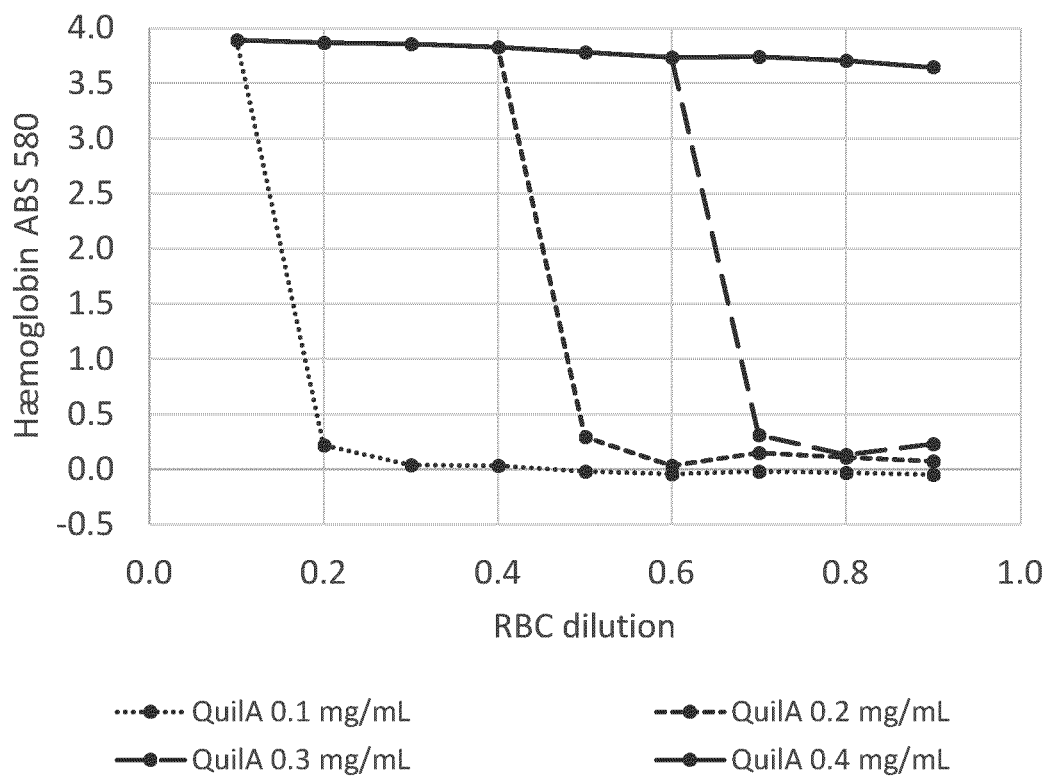

FIG.11
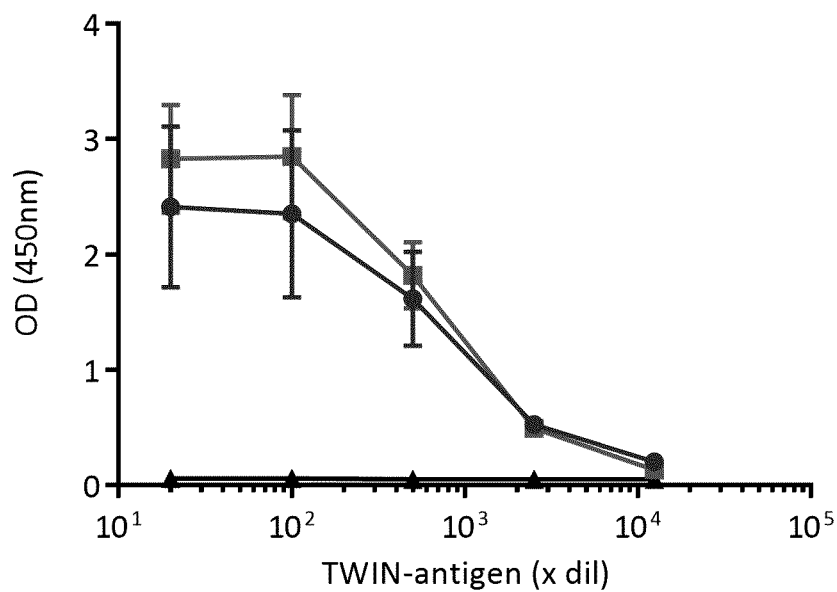
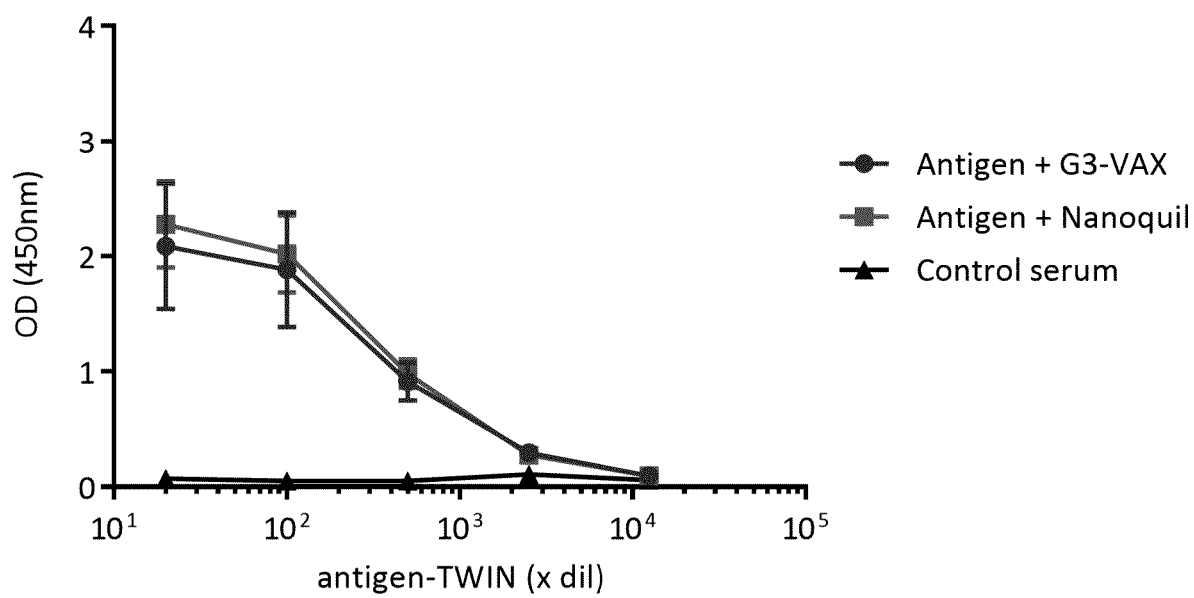

FILAMENTOUS NANOPARTICLES HAVING VACCINE ADJUVANT EFFECT

TECHNICAL FIELD

The present invention relates to filamentous or thread-like nanoparticles comprising sterol and a triterpenoid saponin, such as a component derived from *Quillaja saponaria* Molina selected from quillaja saponins. More particularly, the invention relates to the use of said filamentous nanoparticles in vaccines, cancer therapy and drug delivery, methods for their production and uses thereof, such as for both human and veterinary use as a vaccine adjuvant.

BACKGROUND OF THE INVENTION

Vaccines require optimal adjuvants including immunopotentiator and delivery systems to offer long term protection from infectious diseases in animals and man. Oil emulsions, lipopolysaccharides, polymers, saponins, liposomes, cytokines, immunostimulating complexes (ISCOMs), Freund's complete adjuvant, Freund's incomplete adjuvant, alums, bacterial toxins etc., are common adjuvants under investigation or already implemented in licensed vaccines. Saponin based adjuvants have the ability to stimulate the cell mediated immune system as well as to enhance antibody production and have the advantage that only a low dose is needed for adjuvant activity.

ISCOM-matrices are a series of structurally defined spheroïdal, hollow, cage-like self-assembled nanoparticles (40-60 nm, as observed with Dynamic Light Scattering (DLS)) resulting from the interaction between Quillaja saponins and cholesterol, in a system also containing phospholipids. They exhibit a negative electrostatic charge with a measured $\zeta$-potential of about −30 mV. The combination of an ISCOM-matrix with an antigen is called ISCOM. It is believed that Quillaja saponins (and possibly all saponins with a triterpenoid core) possess a high affinity for cholesterol which induces structuration and stabilization of the ISCOM-matrix.

ISCOMs have been widely explored for antigen delivery as it mimics a virus particle in terms of size and shape (Barr, 1998). ISCOMs high immune response is mainly associated with the presence of QS (*Quillaja saponaria*) saponins, in particular the acylated components such as QS-21, which exhibit strong immunostimulatory activity (Boyaka et al., 2001). This in combination with the particular nature of ISCOMs gives the overall adjuvant effect, and have been reported to induce both humoral and cellular immune responses (Sun et al., 2009).

The biggest challenge with the manufacture of ISCOM is linked to the "solubilization" of cholesterol in the aqueous phase, as this molecule is essentially insoluble in water. The basic idea behind the formation of ISCOM is to provide cholesterol to the bulk solvent in the form of mixed micelles or integrated into vesicles formed by co-detergents or phospholipids. Addition of a micellar solution of Quillaja saponins results in a re-distribution of cholesterol molecules into the saponins micelles, and re-organization of the molecules into the characteristic ISCOM particles. However, this process yields in practice variable results in terms of population homogeneity and number of particles. Therefore, multiple down-stream steps of purification are necessary to eliminate aggregated or residual cholesterol and phospholipids (e.g. phosphatidyl choline), through centrifugation, ultrafiltration, tangential flow or dialysis. Such techniques necessarily cause loss of material during the production process. More detrimental to the large-scale production of ISCOM is the use of pharmaceutical-grade phospholipids (and sometimes co-detergents) which further increases the costs of fabrication. Losses of expensive semi-synthetic cholesterol (from non-animal source) also results in the soaring of production costs. Taken together, these variations in yields and losses become serious hurdles for the large scale production of affordable saponin-based adjuvant nanoparticles.

Some of the formulation problems associated with ISCOM production have been addressed by Morein et al. by the discovery of a new phospholipid-free preparation method resulting in the so-called "G3" saponin based nanoparticles, which are described i.a. in international patent applications WO2013051994 and WO2014163558. However, said preparation method has unfortunately also proven difficult to implement in commercial scale as the obtained product shows heterogenous and variable particle size distribution, and has now been demonstrated by the inventors of the present invention to actually produce particles of a different morphology than that described in the two patent applications.

The present inventors have worked intensively with the attempted scale-up of the procedures described in WO2013051994 and WO2014163558, but realized that the "G3" nanoparticles described in the patent applications and appearing as circular spots of ~20 nm on electron micrographs could not be reproduced by following the instructions in the applications. This was first realized when the obtained products were analyzed not only by transmission electron microscopy (TEM) as employed in the two patent applications, but also by Dynamic Light Scatter (DLS), and Atomic Force Microscopy (AFM). The problem was simply that the claimed 20 nm particles were only visible by TEM analysis, but not with DLS nor AFM.

The analytical techniques differ significantly in their methodology and in their pre-analysis sample preparation. In TEM, a few microliters of the colloidal solution (in phosphate saline buffer, PBS) is deposited onto a metallic grid and dried under vacuum before being sputtered with a contrast agent and visualized with the electron beam. Regions of high electronic density (high molecular density) are observed as projection in a 2D plane. In AFM, a few microliters of sample are deposited onto an atomically flat substrate (freshly cleaved mica sheet), dried and scanned with a resonant AFM tip only a few nanometers thick. The resulting image gives a topology of the surface of the substrate and where the particles on the surface appear in 3D. In particular, the thickness of the particles can be measured. In DLS the sample is analyzed as such (i.e. without drying), dissolved in a phosphate buffer, and a statistical description of the particle size distribution is given. In AFM imaging, the "G3" particles appeared as an heterogenous population of different sizes and shapes, sometimes spheroidal, sometimes elongated along one axis (worm-like) with sizes up to several 100s of nm long, and only a 4 nm to 10 nm thick, never uniformly spherical with a regular diameter between 20 nm and 30 nm. In DLS, the average size distribution was consistently in the range of 50 nm to 60 nm, not 20 nm as claimed in WO2013051994 and WO2014163558. The present inventors therefore speculated if what was observed in TEM as "G3" particles of ~20 nm in WO2013051994 and WO2014163558 could be ascribed to an artifact in the sample preparation. This was corroborated by analyzing a sample by TEM containing no cholesterol or saponin but just the phosphate buffer, which produced a TEM image practically identical to the FIG. 1A of the "G3" particles disclosed in WO2013051994, see FIG. 1. This proved that the "G3" nanoparticles having a diameter of app. 20 nm as described in the two patent applications (see eg FIG. 1A of WO2013051994), were actually phosphate salt crystals or aggregates precipitating from the buffer system upon evaporation of the sample, or formed by interaction with the metallic substrate grid (phosphate ions have affinity for metal surfaces). Control observations of the same buffer system alone or of saponin-cholesterol particles (real "G3" particles) in the buffer system deposited on carbon substrate grids instead of metallic grids never yielded the disk-shaped structures of ~20 nm in diameter reported in the patent applications, proving their artifactual nature. By DLS no such particles were visible, since the phosphate salts are dissolved under the analysis conditions.

The inventors of the present invention decided to investigate the nature and/or morphology of the "G3 particles" described in WO2013051994 and WO2014163558 closer, since the preparations had after all demonstrated biological effects i.a. in different inoculation experiments. To this end, the original procedure as disclosed in WO2013051994 was carried out 5 times and the resulting particles analyzed by DLS. The result was that the original procedure afforded particles having a heterogenous particle size distribution for the individual experiment (see FIG. 2) and further a large variability between the experiments. It was concluded that this lack of homogeneity was unacceptable for a commercial adjuvant.

Thus, there remains a need for developing a reliable and scalable procedure for saponin-based nanoparticles, which may be used as carrier/delivery particles for pharmaceuticals and as vaccine adjuvants.

SUMMARY OF THE INVENTION

The inventors of the present invention have now found that both the morphology and the size distribution of the particles obtained by the original manufacturing procedure as disclosed in WO2013051994, can be drastically modified by changing a few critical reaction parameters; in particular by incubating the particles at an elevated temperature and adjusting the ratio between saponin and cholesterol in the initial preparation. In contrast to the particles depicted in the DLS graph of FIG. 2, which shows two or more types of particles of different apparent sizes, particles produced according to the method of the present invention have a uniform size when measured by DLS (mono-dispersed, see FIG. 4).

Accordingly, in a first aspect of the present invention, there is thus provided nanoparticles comprising cholesterol and a triterpenoid saponin, such as a component from *Quillaja saponaria* Molina such as Quil AR or components isolated therefrom, such as fractions QS-7, QS-8, QS-17, QS-18 and QS-21, or a component from *Quillaja brasiliensis*, such as fraction QB-90, characterized in that said nanoparticles are thread-like (filamentous). These nanoparticles are henceforth referred to throughout the present application as "NanoQuil F70" particles.

In a second aspect the present invention provides a method for producing the NanoQuil F70 nanoparticles of the first aspect, comprising the following steps:
a) Prepare a layer of cholesterol on the inner surface of a reaction vessel and/or on the surface of a water-insoluble, porous article located in said reaction vessel, by removing the solvent from a non-aqueous solution of cholesterol in an organic solvent selected from one or more $C_1$-$C_6$ alcohols, $C_2$-$C_6$ ketones, $C_1$-$C_6$ alkyl esters of $C_1$-$C_3$ carboxylic acids, and linear or cyclic $C_4$-$C_8$ ethers,
b) Add an aqueous reaction medium, which may be a solution of one or more salts, a buffer solution, or salt-free distilled water, preferably pre-heated to 70° C.±5° C.,
c) Add a solution of triterpenoid saponins, such as a Quillaja saponin to a final concentration of 1 mg/ml to 10 mg/ml to produce a final ratio of 10:1 to 20:1, preferably 16:1 (w/w) saponin: Cholesterol,
d) Heat the reaction mixture at 70° C.±5° C. for about an hour,
e) Cool the reaction mixture to 4° C.±2° C. overnight, isolate the formed particles and remove excess saponin e.g. by size exclusion chromatography (SEC).

The "NanoQuil F70" nanoparticles prepared by the method according to the second aspect of the present invention differ substantially from the prior art, including the so-called "G3" nanoparticles described in WO2013051994 and WO2014163558, not least by their unique combination of morphology (thread-like (filamentous) shape vs. round/spherical) and particle dispersion (uniform vs. non-uniform) when measured by DLS analysis.

Comparing the method steps of the procedure as disclosed in WO2013051994 with those of the present invention, it is clear that the structural characteristics which define the NanoQuil F70 nanoparticles of the second aspect are due to the modifications of the manufacturing procedure vis-à-vis the procedure described in WO2013051994 and WO2014163558.

The nanoparticles according to the invention may be used as delivery systems for one or several compounds e.g. for pharmaceuticals including those used for treatment of cancer and nutrition related compounds where the additional substance(s) provide additional functions and complementary modes of action.

In a third aspect the NanoQuil F70 nanoparticles and compositions comprising them may be used as such as a pharmaceutical, optionally in a pharmaceutical composition further comprising pharmaceutically acceptable buffers, diluents excipients, additives, adjuvants and/or carriers. Amphipathic and hydrophobic molecules, which may be selected from an antigen, an adjuvant, a targeting molecule, a pharmaceutical compound and a nutriment may be integrated into the nanoparticles according to the present invention, or mixed therewith in a composition. Alternatively different compounds are incorporated into separate nanoparticles. The pharmaceutical composition may be used as an adjuvant, e.g. for use in combination with a vaccine, for use in combination with a seasonal influenza virus vaccine, for use in combination with a pandemic influenza vaccine or for use in combination with an emergency vaccine, such as a vaccine against a biological weapon.

Thus, the invention also regards a pharmaceutical vaccine formulation comprising the NanoQuil F70 particles according to the present invention, especially as an adjuvant, as mentioned above.

The invention also relates to a method for treating or preventing a disease caused or complicated by an organism, comprising administering to a subject a pharmaceutical vaccine formulation according to the invention to a person in need thereof.

Further, the invention regards a method for treatment of cancers, including solid tumors, comprising administering to a patient in need thereof a pharmaceutically effective amount of NanoQuil F70 nanoparticles or a composition containing them, according to the present invention.

Further, the invention also regards NanoQuil F70 nanoparticles, or a composition containing them, for use in the treatment of cancers, comprising administering to a patient in need thereof a pharmaceutically effective amount of NanoQuil F70 nanoparticles or a composition containing them.

The therapeutic effect of both the G3 particles mentioned hereinabove and of the NanoQuil F70 nanoparticles of the present invention on various types of cancer cells is thought to be caused by the ability of the nanoparticles to transform cancer cells into apoptotic cells by terminating the mitotic cycle.

The NanoQuil F70 nanoparticles, or compositions containing them may be administered parenterally. The term parenteral as used herein includes subcutaneous injections, intravenous, intramuscular, intradermal injection of infusion techniques, electroporation (EP), for needle less injection-jet injection, gene gun, biljector as well as oral, aerosol administrations.

The invention also regards a method for assessing the applicability of the method for treatment of cancer according to the invention to an individual patient, comprising
bringing cancer cells from said patient in contact in vitro with NanoQuil F70 nanoparticles according to the present invention or a pharmaceutical composition containing such nanoparticles,
measuring at least one effect indicative of therapeutic effect of said nanoparticles or pharmaceutical composition, on said cancer cells;
wherein the method is assessed as being applicable to said individual patient if the nanoparticles or pharmaceutical composition shows a significant effect indicative of therapeutic effect on said cancer cells.

Differences in particle size (hydrodynamic diameter) were observed by DLS in these formulations: NanoQuil F70 formulated in PBS gives the biggest size (about 42 nm), followed by NanoQuil F70 formulated in Saline solution (about 35 nm). NanoQuil F70 particles formulated in Acetate buffer (pH 4.6) and distilled water give particle sizes of around 25 and 24 nm respectively.

Figure 1A:
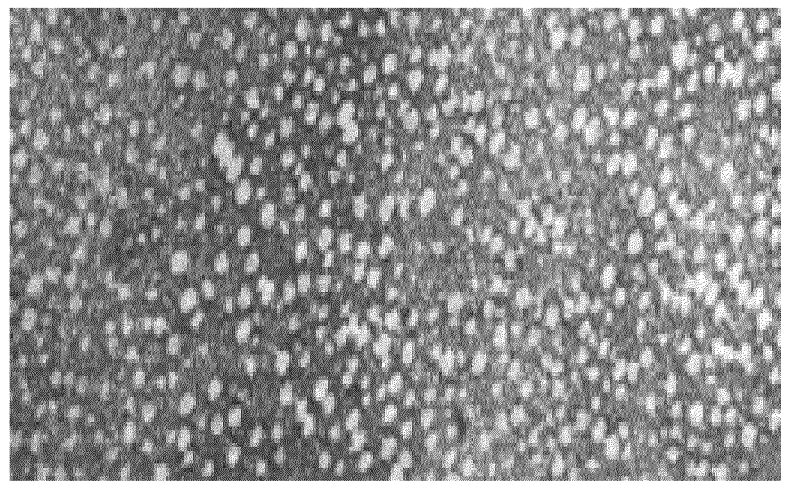
FIG. 1A: A copy of FIG. 1A from WO2013051994 which is described as "The electron microscopy (EM) shows a nanoparticle comprising cholesterol, QHC and diterpenoid in a molar ratio of 1:1:0.5. The particles have a mean diameter of about 17-20 nm according to the invention".
Figure 1B:
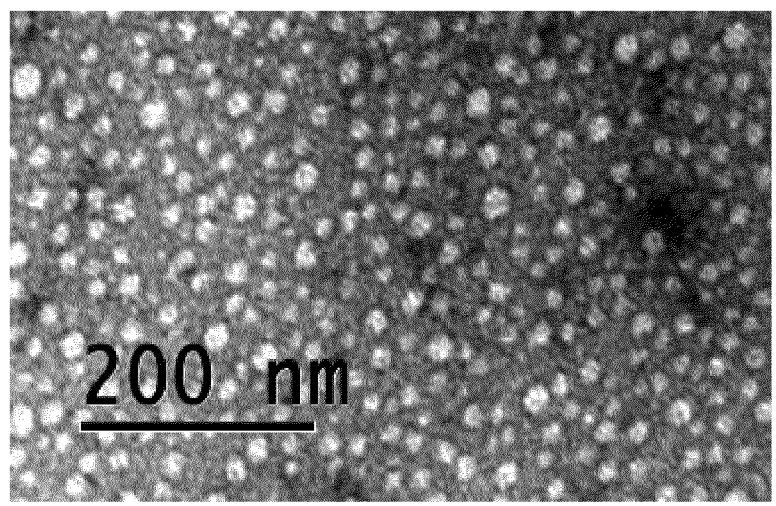
FIG. 1B: An electron microscopy of a sample containing no cholesterol or saponin but just the phosphate buffer. The 20 nm "nanoparticles" caught on this TEM photo after a similar sample preparation as for FIG. 1A, are just phosphate salts which precipitate during the required evaporation of the phosphate buffer.
Figure 2:
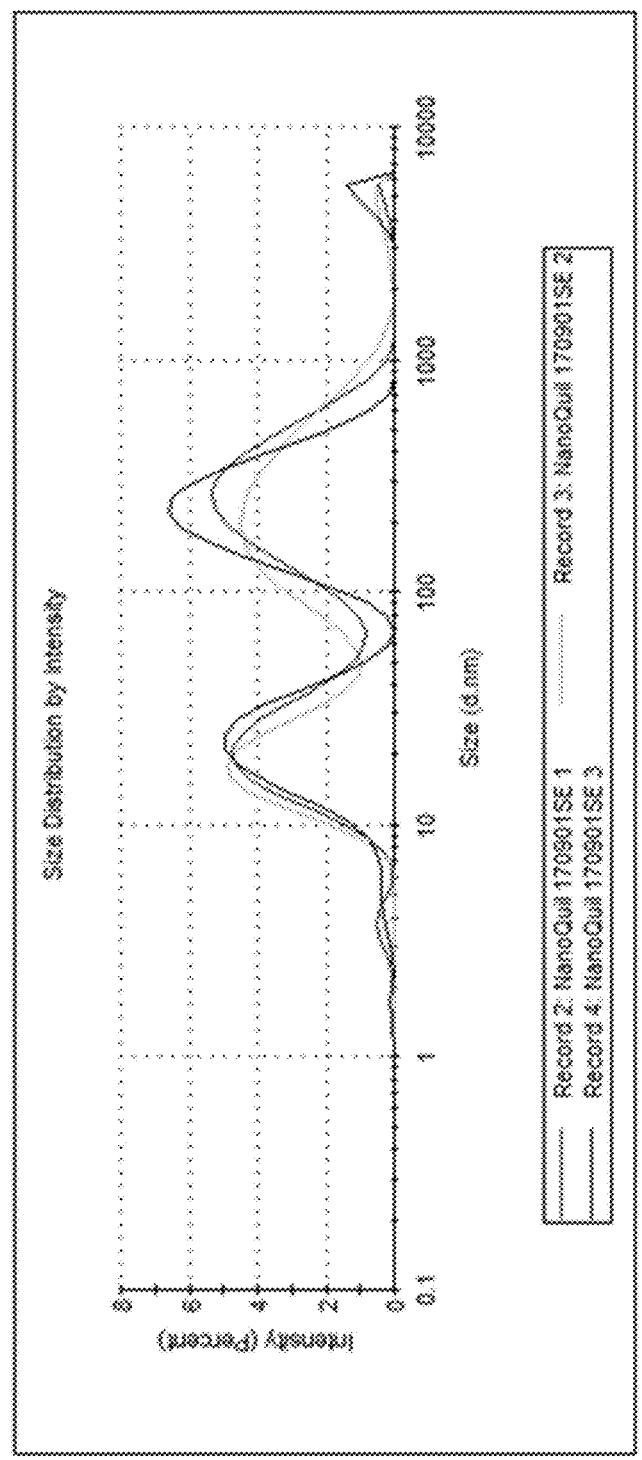
FIG. 2: DLS particle size analysis of 3 batches produced according to the procedure described in WO201305199. As can be seen, the particles contain at least two main fractions.
Figure 3A:
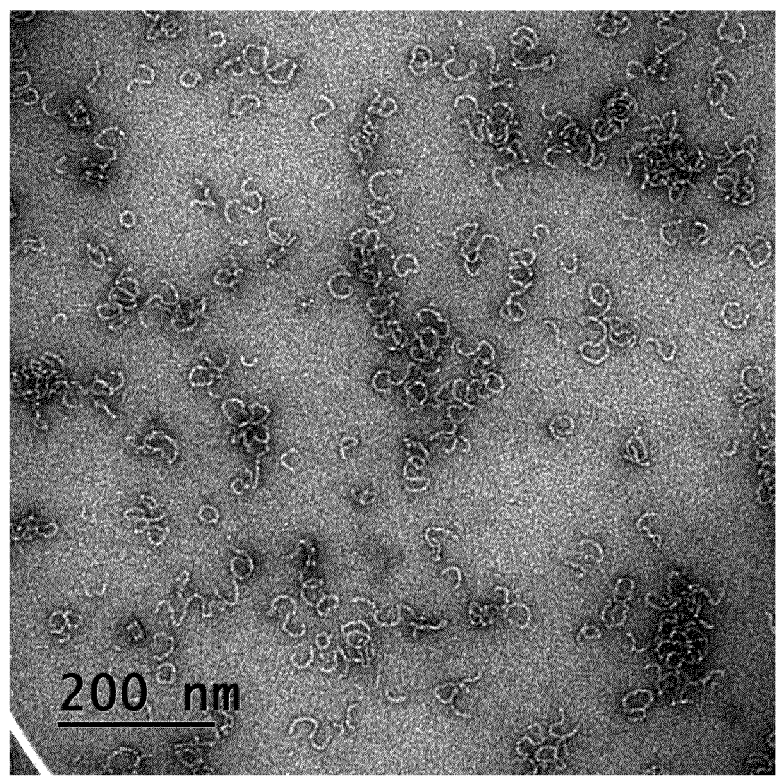
FIGS. 3A and 3B: Transmission Electron Microscopy of NanoQuil F70 particles according to the invention using either PBS (FIG. 3A) or distilled water (FIG. 3B) as the aqueous reaction medium, and an incubation period of about an hour at 70° C. The TEM photos reveal that regardless of the reaction medium, the resulting F70 particles have a filamentous (thread-like) shape, i.e. a completely different morphology than that of the alleged disc-like nanoparticles of WO2013051994.
Figure 3B:
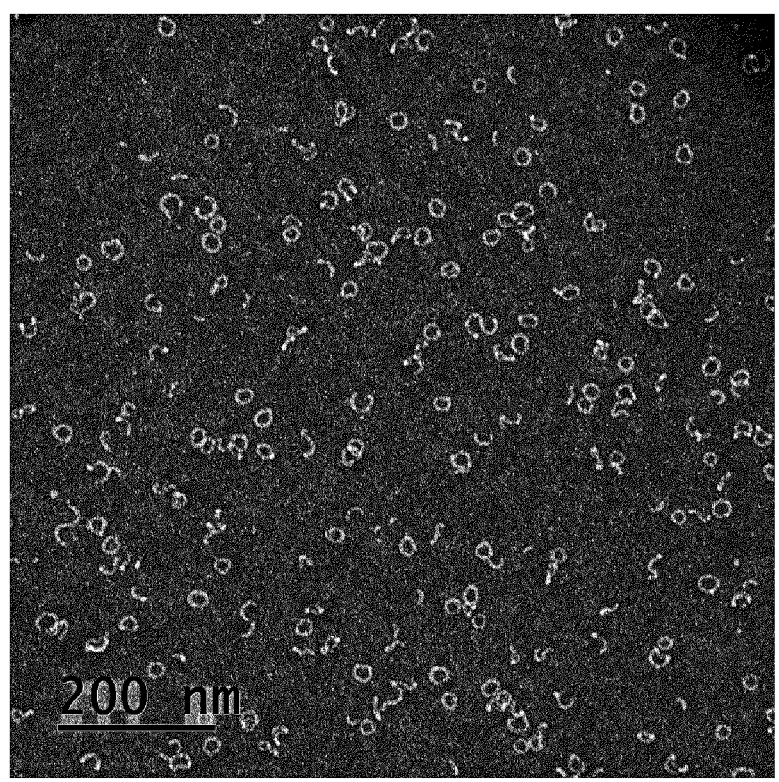
Figure 3C:
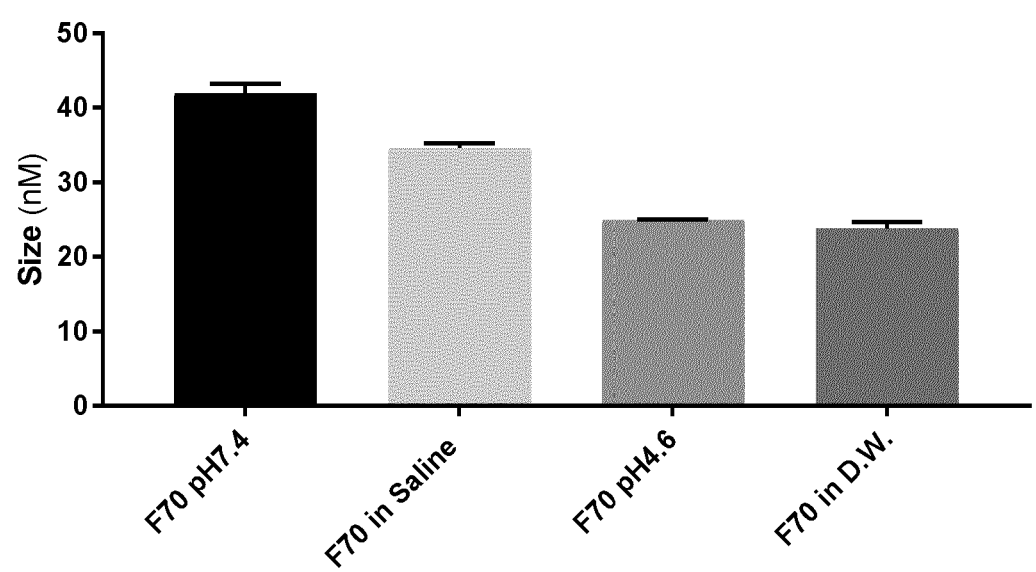
FIG. 3C: Bar chart showing NanoQuil F70 nanoparticles produced using 4 different aqueous reaction media: Distilled water (D.W.), Saline solution (0.85% NaCl in D.W.), Acetate buffer (pH 4.6) and PBS (pH 7.4) according to the above NanoQuil F70 production protocol.
Figure 4:
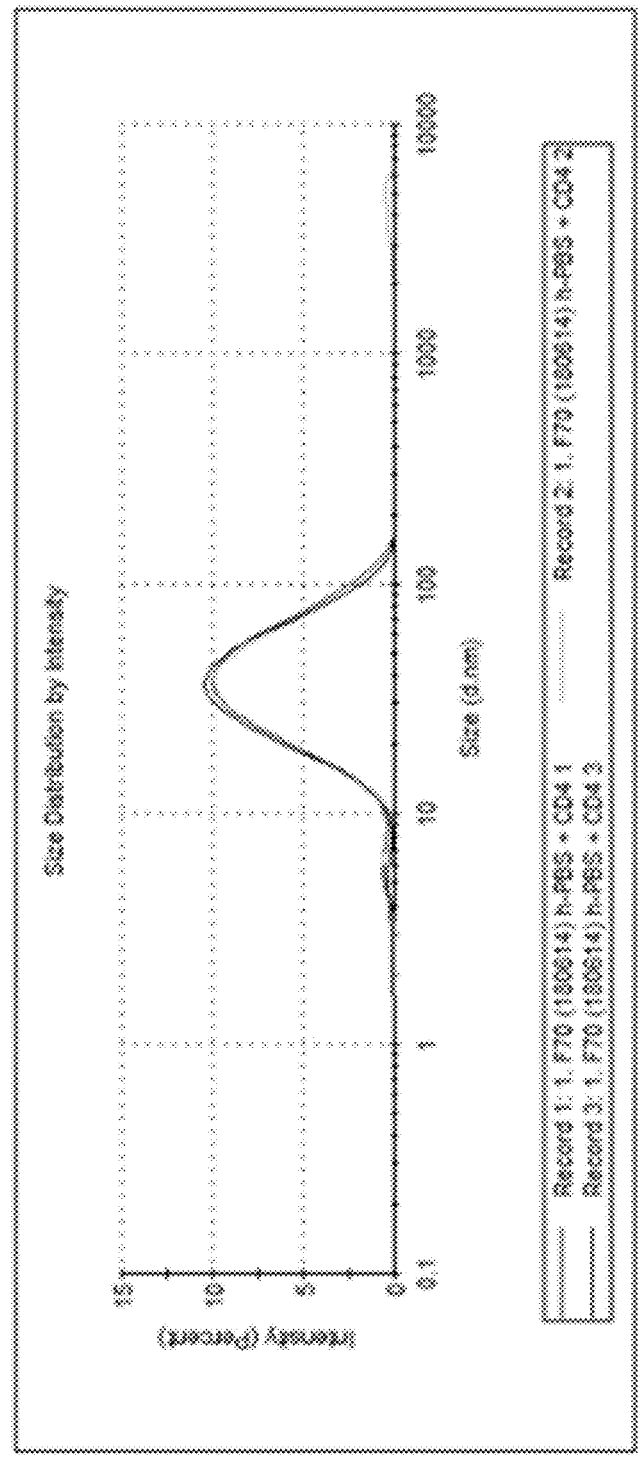

FIG. 4: The same particles as TEM-analyzed in FIG. 3A, now analysed for particle size distribution by DLS. This reveals that the particles according to the present invention are monodispersed with an average hydrodynamic diameter of 42.2 nm±1.0 nm when prepared in PBS. For particles produced in other media than PBS, see FIG. 3C.

FIG. 5: The Dynamic Light Scattering (DLS) analysis of three batches of NanoQuil F70 prepared in PBS, before purification by SEC.

Figure 6:
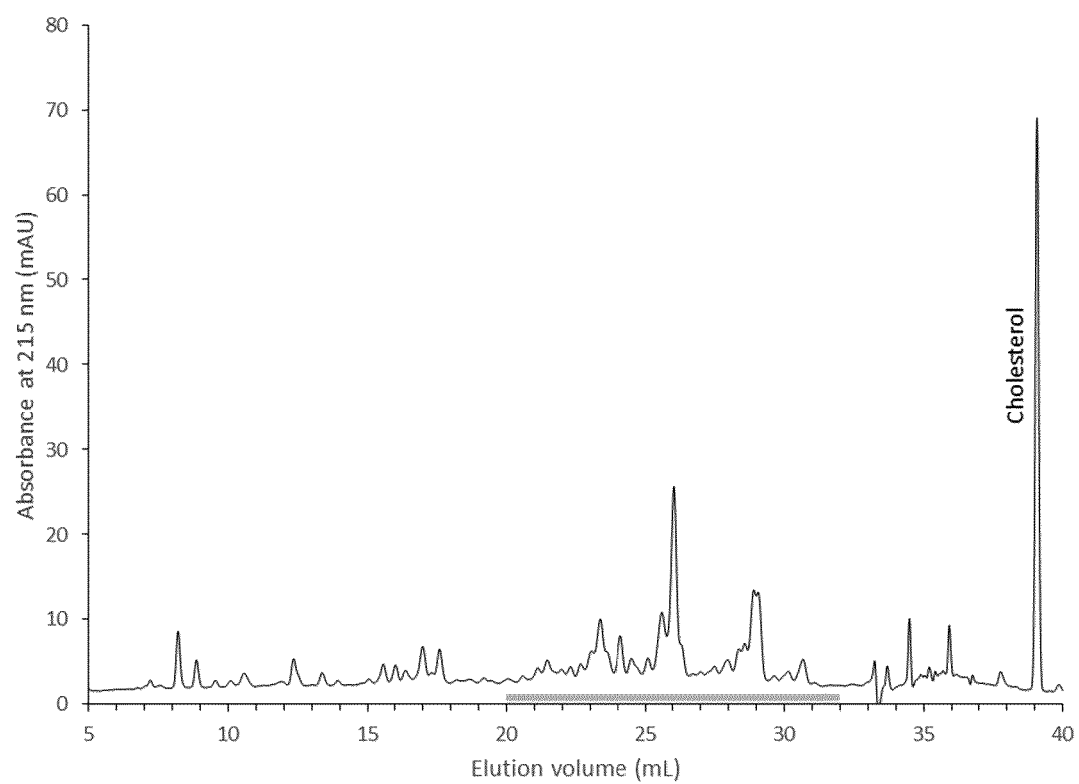

FIG. 6: RP-HPLC chromatogram of NanoQuil F70 purified by SEC on Sephacryl S300-HR. The fraction eluting at 6 mL from the 13 mL Sephacryl S300-HR cartridge and containing purified NanoQuil F70 was analyzed by HPLC. Integration of the signal between 20 ml and 32 mL (grey bar) is used to quantify the saponins in the fraction. Integration of the signal at 39 mL is used to quantify cholesterol.

Figure 7:
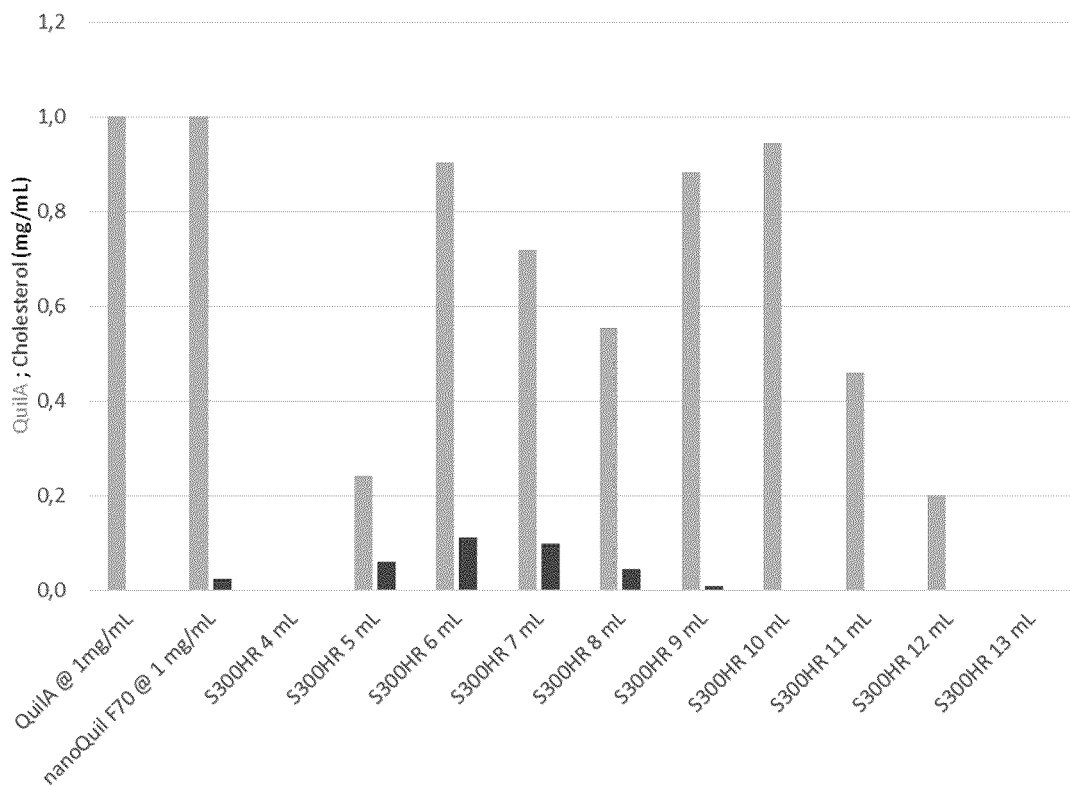

FIG. 7: Relative quantities of QuilA (light grey) and cholesterol (dark grey) collected in the SEC fractions. A volume of 1 mL of NanoQuil F70 at 4.2 mg/ml QuilA was loaded onto the Sephacryl S300-HR column and 1 mL fractions were collected for HPLC quantitative analyses. SEC fractions containing detectable amounts of QuilA, from 4 mL to 13 mL are shown. NanoQuil F70 and QuilA are shown as references.

Figure 8:
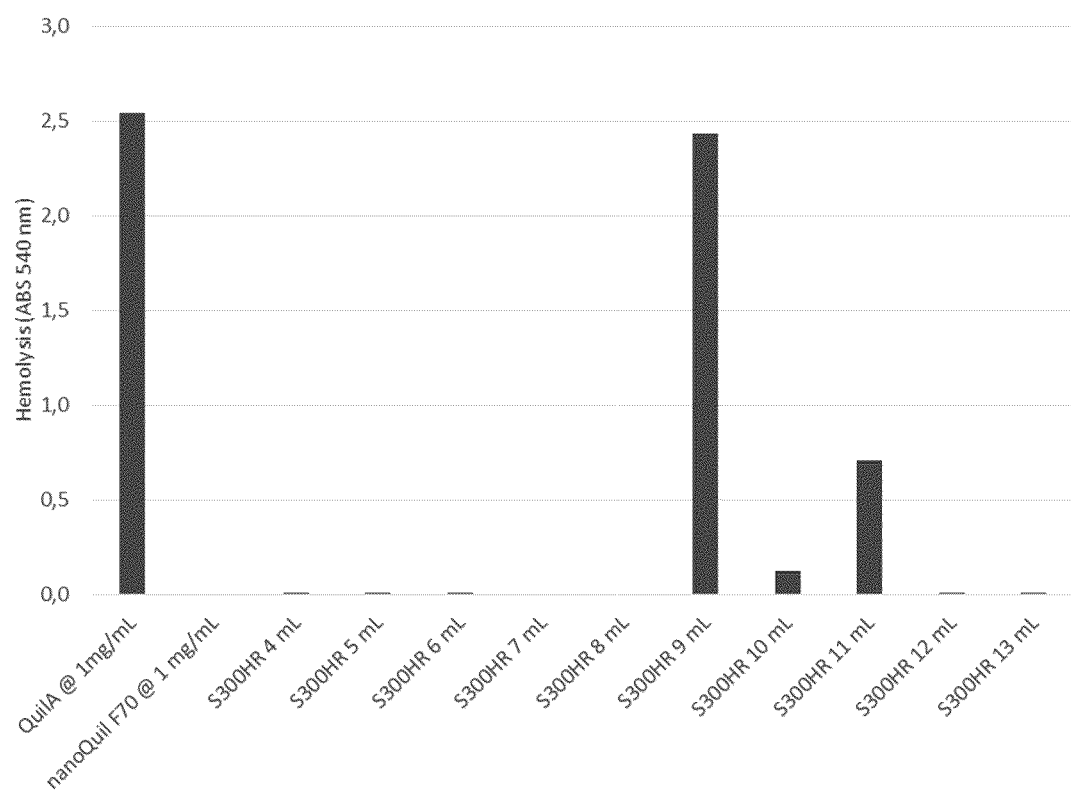

FIG. 8: Hemolytic effect of sephacryl S300-HR SEC fractions of NanoQuil F70.

FIG. 9: Hemolytic assay with QuilA alone. Graph shows the released hemoglobin from red blood cells (RBC) as a function of RBC dilution.

At 0.4 mg/mL, QuilA shows full hemolytic potential in this assay. Reduction in hemolytic effect is observed from 0.3 mg/ml down.

Method: 20 μL of QuilA was added to 180 μL of fresh sheep blood diluted from 0.9× to 0.1× in PBS. Mixtures were incubated at 37° C. for 45 min, and cells are pelletted at 500×g for 5 min. Hemoglobin in the supernatant is measured by measuring the absorbance at 580 nm.

Figure 10A:
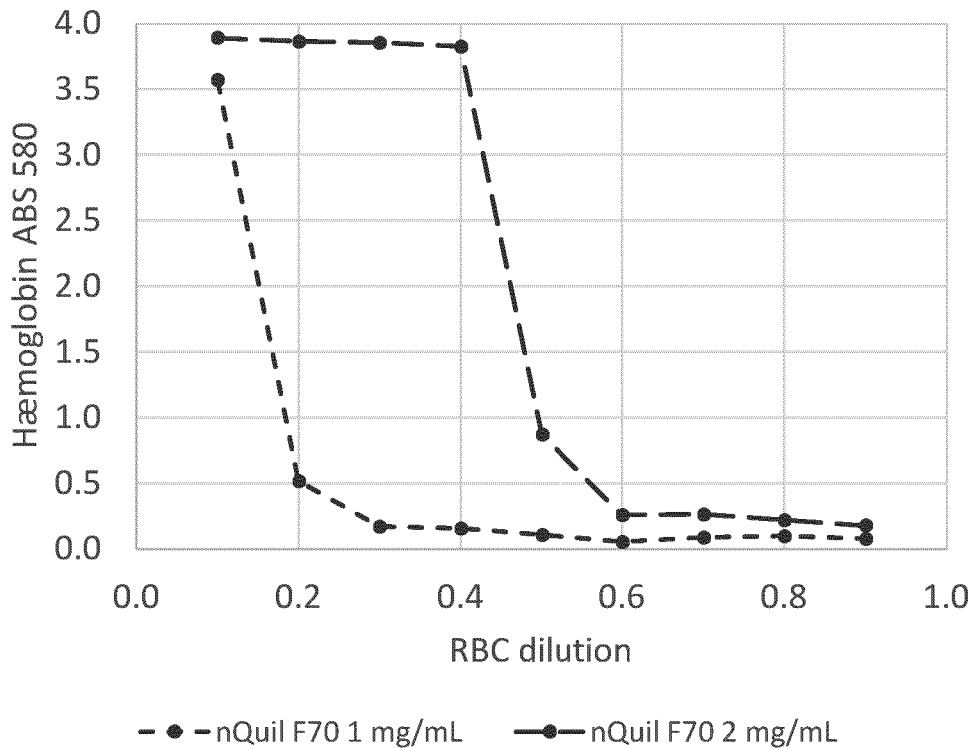
Figure 10B:
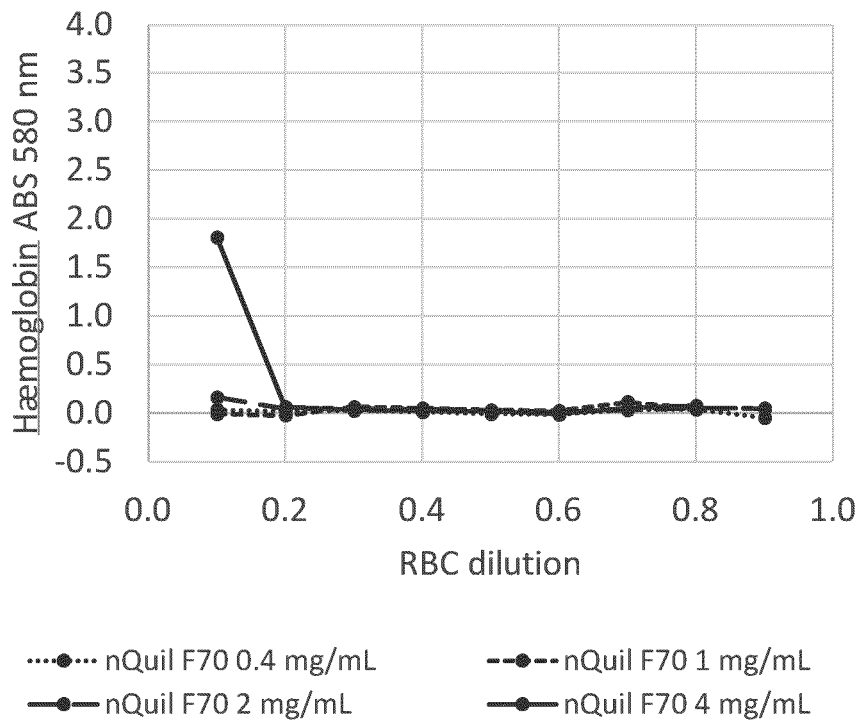

FIGS. 10A and 10B: Hemolytic assay with nanoQuil F70 particles. Graph shows the released hemoglobin from red blood cells (RBC) as a function of RBC dilution. Test method as for FIG. 9.

FIG. 10A: In comparison to QuilA alone (FIG. 9), unpurified (raw) nanoQuil F70 shows hemolytic effect at an equivalent QuilA concentration of 1 mg/mL. At 2 mg/ml raw nanoQuil F70, the hemolytic effect is similar to that induced by 0.2 mg/ml free QuilA.

FIG. 10B: S300-HR purified nanoQuil F70 does not show hemolytic effect until an equivalent QuilA concentration of 2 mg/mL. At 4 mg/ml purified nanoQuil F70, the hemolytic effect is lower or similar to that induced by 0.1 mg/ml free QuilA or by 1 mg/ml raw nanoQuil F70.

FIG. 11: A comparison of the adjuvant effect of nanoQuil F70 particles with G3 particles. No significant difference was found between G3-VAX and Nanoquil particles. However, nanoQuil F70 seemed to generate slightly more potent ab responses and less variation than G3.

Figure 12:
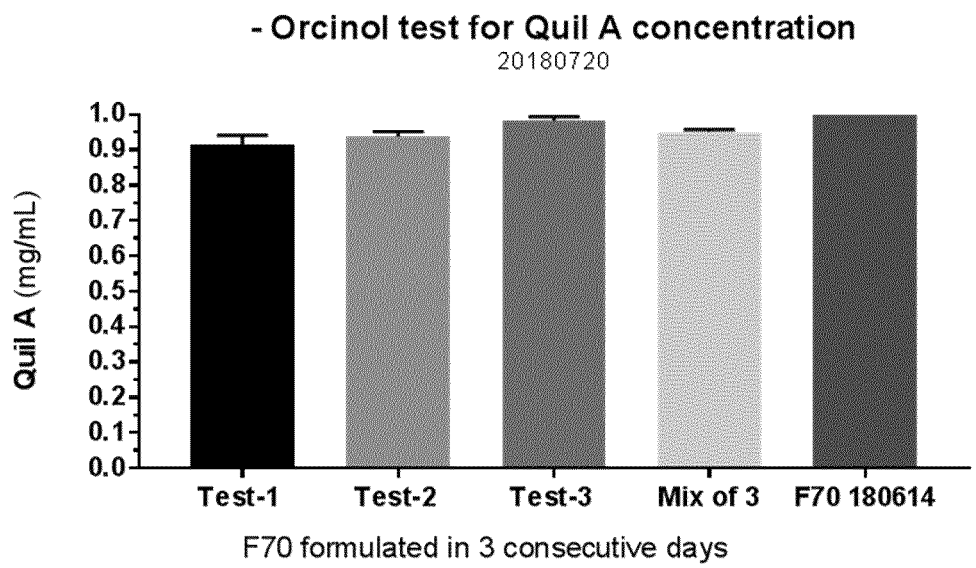

FIG 12: Quil A content of the produced NanoQuil F70 nanoparticles was measured using the Orcinol test.

Figure 13:
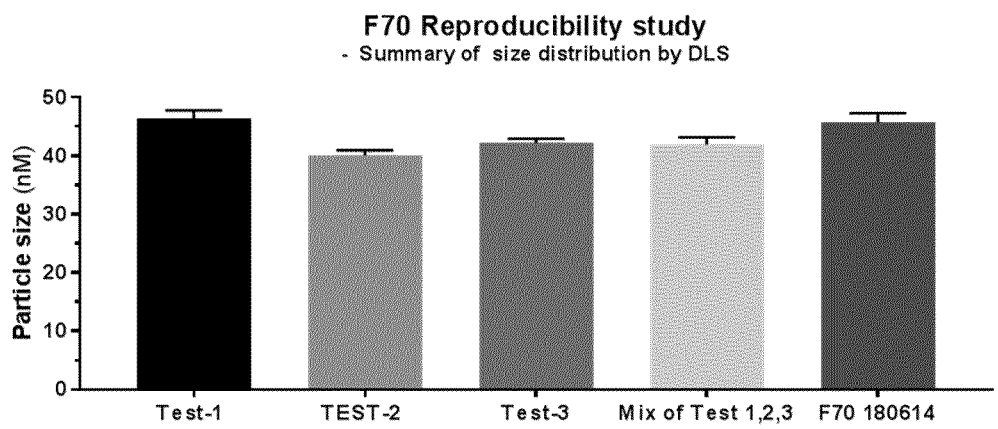

FIG. 13: A graphic summary of the DLS measurements of FIG. 5 of the mean particle sizes of the three formulations is shown.

Figure 14:
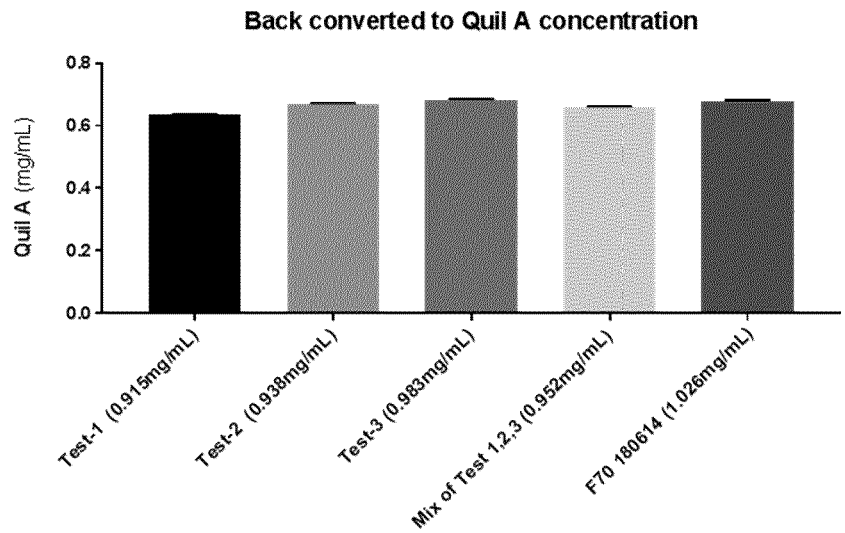

FIG. 14: A bar chart of the hemolysis reduction rates for the three batches (Test-1, -2 and -3) of NanoQuil F70 is shown.

Figure 15:
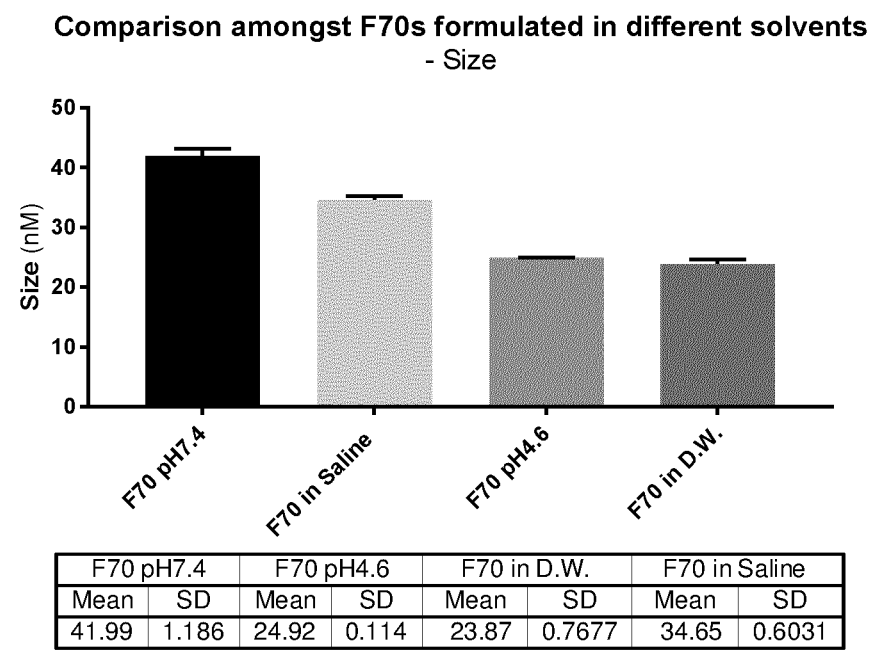

FIG. 15: A bar chart of particle sizes of NanoQuil F70 particles formulated in different solvents is shown.

Figure 16:
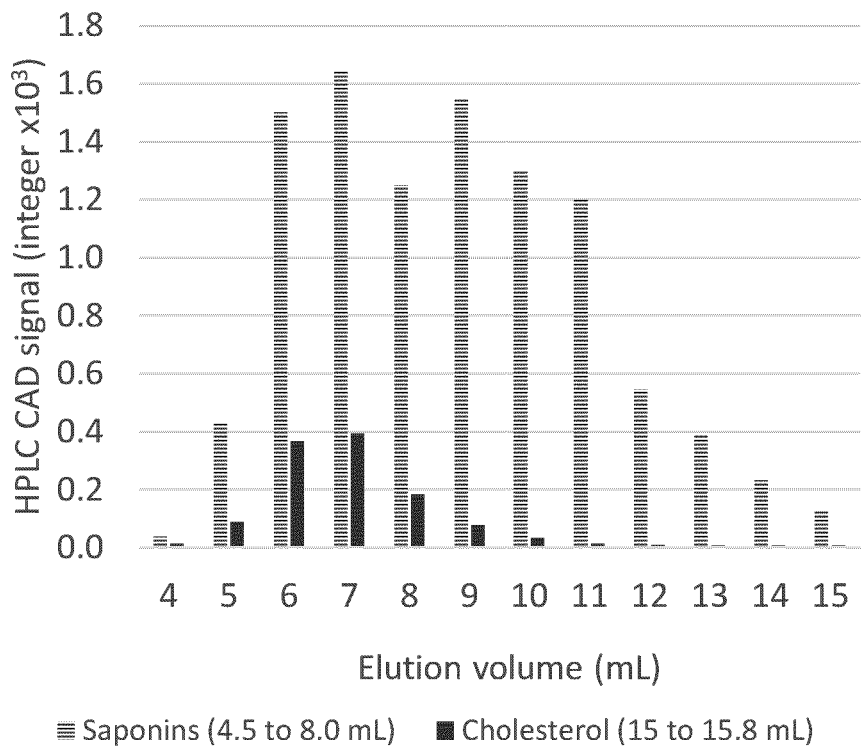

FIG. 16: An integrated CAD signal for the S300HR fractions corresponding to the sum of saponins peaks and the cholesterol peak is shown.

Figure 17:
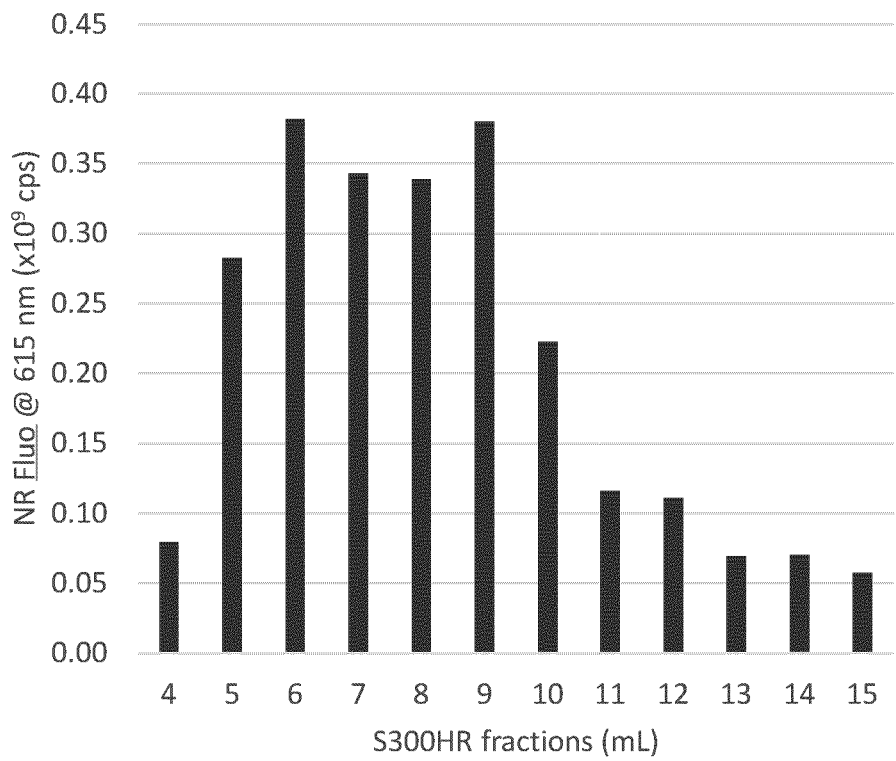

FIG. 17: A bar chart of the distribution of saponins in the S300HR SEC fractions using the fluorophore Nile Red is shown.

Figure 18:
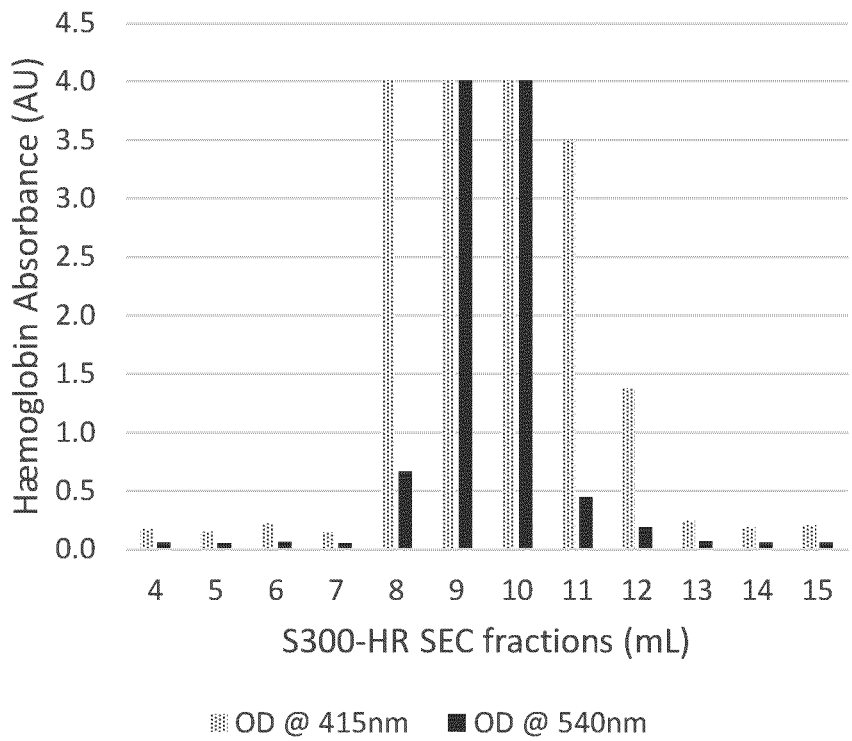

FIG. 18: A bar chart of the hemolytic activity of the NanoQuil F70 SEC fractions expressed as a function of the absorbance value at 540 nm against a calibration range with QuilA saponin from 0.4 mg/mL to 1.0 mg/mL is shown.

Figure 19:
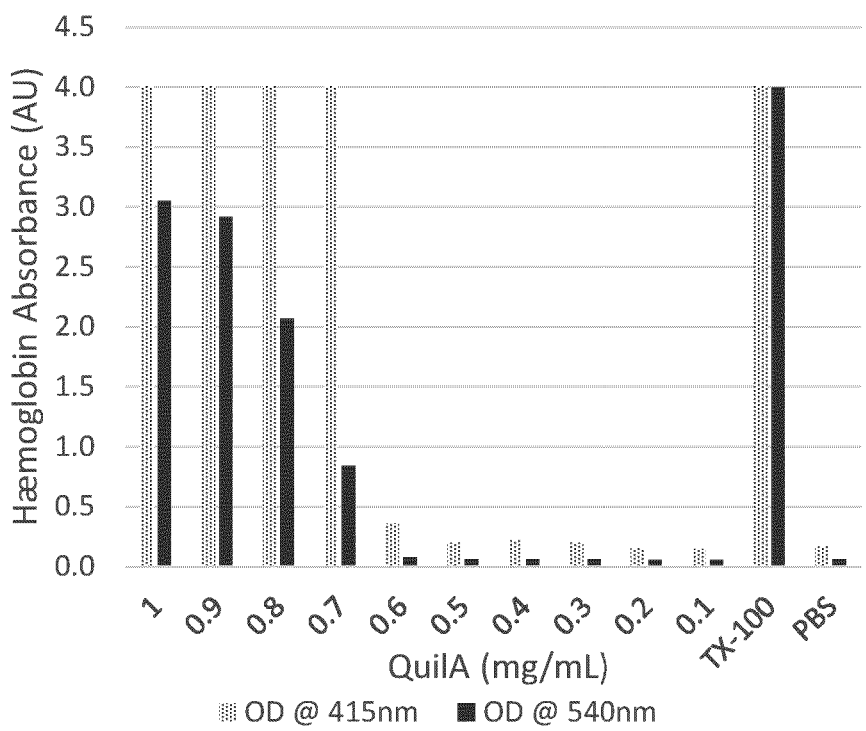

FIG. 19: A bar chart shows as "equivalents QuilA" that the most hemolytic S300-HR fractions (9 mL and 10 mL) are those containing free QuilA, whereas fractions 6 mL and 7 mL containing nanoQuil F70 do not show a hemolytic effect.

Figure 20:
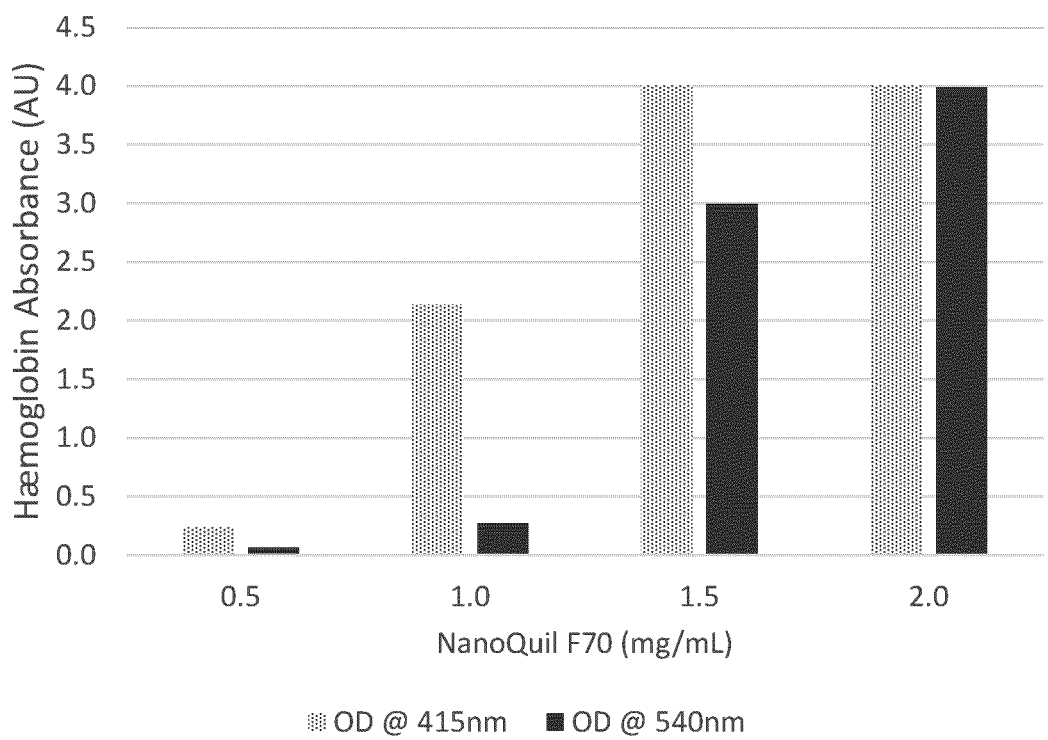

FIG. 20: A bar chart of the raw nanoQuil F70 product shows a hemolytic effect from 1 mg/mL equivalent QuilA and up.

DEFINITIONS

All terms and words in the present specification shall be construed as having the meaning usually given to them in the relevant art unless specifically indicated otherwise. For the sake of clarity, a few terms are defined below.

A vaccine formulation is a pharmaceutical formulation that is used prophylactically and improves/enhances protective immunity to/against one or more particular diseases.

A therapeutic vaccine according to the invention can be used to cure or treat disease when an antigen specific for a component connected to the disease is included in the formulation with the invention or, as is particular for cancer treatment, the antigen is present in the cancer/tumor. A vaccine includes an "antigen" that elicits an immune response in the treated subject and, optionally, a substance added to a vaccine to improve the immune response called an "adjuvant" or "immunostimulator".

An "antigen" is thus the active specific part in a vaccine and may be the entire micro-organism, such as virus or bacteria, causing the disease that the vaccine is aimed at improving immunity to. It may also be a part of said micro-organism a subunit, such as a protein (a sub-unit) a part of a protein, a protein either isolated from the pathogenic microorganism or produced by rDNA technique or synthetically produced then often called peptide. A peptide has fewer amino acids than a protein and generally no ordered 3D structural fold.

An "adjuvant" is a vaccine constituent that enhances the level and/or the quality of the immune response to the antigen part of the prophylactic or therapeutic vaccine.

DETAILED DESCRIPTION OF THE INVENTION

The inventors have discovered that the observed heterogeneity (when analysed by Dynamic Light Scattering, DLS) of the particles prepared according to the procedure of WO2013051994 surprisingly can be overcome by incubating the particles at an elevated temperature and adjusting the ratio between saponin and cholesterol in the initial preparation. Other process parameters, such as the surface area and thickness of the cholesterol film and the solvent polarity may also play a role. The morphology of the "NanoQuil F70" particles produced by the procedure according to the present disclosure differs from the morphology of the apparent disc-shaped "G-3" particles produced by the procedure disclosed in WO2013051994, in that the NanoQuil F70 particles according to the present disclosure are filamentous, "thread-like", and can appear either open-shaped, i.e. worm- or noodle-like, or closed-shape/circular (in contrast to the apparent disc-shaped form in WO2013051994), see FIGS. 3A and 3B. The NanoQuil F70 nanoparticles according to the present invention are not formulated with, and do not contain, phospholipids or co-detergents (such as MEGA-10), in contrast to, for example, ISCOM and ISCOM matrix adjuvant formulations.

In a first aspect of the present invention, there is thus provided nanoparticles ("NanoQuil F70") comprising cholesterol and a triterpenoid saponin, such as a component from *Quillaja saponaria* Molina such as Quil AR, or components isolated therefrom, such as fractions QS-7, QS-8, QS-17, QS-18 and QS-21, or a component from *Quillaja brasiliensis*, such as fraction QB-90, characterized in that said nanoparticles are thread-like (filamentous).

As mentioned above the nanoparticles according to the first aspect have been found by TEM analysis to exist in two separate forms, both having a characteristic thread-like (filamentous) shape. One form is open-ended, i.e. worm- or noodle-like, the other form is closed, and substantially circular. Nanoparticles produced according to the methods described hereinbelow typically contain both forms.

In an embodiment the NanoQuil F70 nanoparticles may thus comprise two forms:

Form A, composed of closed, substantially circular nanoparticles, and

Form B, composed of open-ended, worm-like nanoparticles.

The ratio of Form A: Form B is influenced by the nature of the employed reaction solvent and/or by the pH of the employed reaction solvent, amongst other parameters.

In a further embodiment said mixture of Form A and Form B has a ratio of from between 20:80 to 45:55, such as 30:70 to 40:60, such as about 35:65.

In another embodiment said mixture of Form A and B has a ratio of from between 5:95 to 10:90. In an embodiment the nanoparticles according to the first aspect are substantially composed of just one form, i.e. the nanoparticles contain at least about 95% of either Form A or Form B.

In another embodiment the substantially circular nanoparticles of Form A have a radius of between 10-15 nm and the open-ended nanoparticles of Form B have a length of 35-45 nm, both values as measured by TEM.

In an embodiment the filament diameter or thickness is between 4-8 nm, preferably 5-7 nm, such as 5.8±0.8 nm.

In another embodiment the substantially circular nanoparticles of Form A have a perimeter of between 65-120 nm, such as 70-80 nm, such as 80-90 nm or such as 85-120 nm.

In another embodiment the substantially circular nanoparticles of Form A have a perimeter of 75±7 nm.

In another embodiment the substantially circular nanoparticles of Form A have a perimeter of 103.5±17 nm.

In another embodiment the ratio between quillaja saponin and cholesterol is from 12:1 to 18:1, such as 14:1 to 17:1, preferably 16:1.

The NanoQuil F70 nanoparticles according to the first aspect of the present invention differ substantially from the prior art, including the so-called "G3" nanoparticles described in WO2013051994 and WO2014163558, not least by their unique combination of morphology (filamentous/thread-like vs. disc-like) and particle dispersion (uniform vs. non-uniform).

Thread-like nanoparticles have attracted considerable interest in the field of drug delivery systems. In a study documented by B. Karagoz et al. "Polymerization-Induced Self-Assembly (PISA)-control over the morphology of nanoparticles for drug delivery applications.", Polym. Chem., 2014 it was shown that cylindrical and worm-like nanoparticles are seven times more deadly than traditional spherical ones when delivering drugs to breast cancer cells, but not more toxic to healthy cells.

These results have been corroborated in another study documented by Elizabeth Hinde et al. in "Pair correlation microscopy reveals the role of nanoparticle shape in intracellular transport and site of drug release", Nature Nanotechnology volume 12, pages 81-89 (2017). Hinde et al. demonstrated that polymeric nanoparticles with different shapes but identical surface chemistries moved across the various cellular barriers at different rates, ultimately defining the site of drug release. The group measured how micelles, vesicles, rods and worms entered the cell and whether they escaped from the endosomal system and had access to the nucleus via the nuclear pore complex. Rods and worms, but not micelles and vesicles, entered the nucleus by passive diffusion. Improving nuclear access, for example with a nuclear localization signal, resulted in more doxorubicin release inside the nucleus and correlated with greater cytotoxicity. The group's results therefore demonstrate that drug delivery across the major cellular barrier, the nuclear envelope, is important for doxorubicin efficiency and can be achieved with appropriately shaped nanoparticles.

In a second aspect of the present invention, there is provided a production method for the filamentous (thread-like) NanoQuil F70 particles of the first aspect, comprising the following steps:
 a) Prepare a layer of cholesterol on the inner surface of a reaction vessel and/or on the surface of a water-insoluble, porous article located in said reaction vessel, by removing the solvent from a non-aqueous solution of cholesterol in an organic solvent selected from one or more $C_1$-$C_6$ alcohols, $C_2$-$C_6$ ketones, $C_1$-$C_6$ alkyl esters of $C_1$-$C_3$ carboxylic acids, and linear or cyclic $C_4$-$C_8$ ethers,
 b) Add an aqueous reaction medium, which may be a solution of one or more salts, a buffer solution, or salt-free distilled water, preferably pre-heated to 70° C.±5° C.,
 c) Add a solution of triterpenoid saponins, such as a Quillaja saponin, to a final concentration of 1 mg/ml to 10 mg/ml to produce a final ratio of 10:1 to 20:1, preferably 16:1 (w/w) saponin: Cholesterol,
 d) Heat the reaction mixture at 70° C.±5° C. for about an hour,
 e) Cool the reaction mixture to 4° C.±2° C. overnight, isolate the formed particles and remove excess saponin e.g. by size exclusion chromatography (SEC).

Regarding point a) of the second aspect, the skilled artisan will understand the importance of achieving an intimate contact between water-insoluble cholesterol and water-soluble saponins in order to produce the NanoQuil F70 particles of the invention. This requires creating a large, solvent-accessible surface of cholesterol. In one embodiment of the invention this is carried out by preparing and/or depositing as thin a layer of cholesterol as possible on the inner surface of a reaction vessel into which the saponin-solution can subsequently be added.

Alternatively, in another embodiment, the layer of cholesterol may be prepared and/or deposited on the surface of a water-insoluble porous article which can be brought in contact with the saponin-solution. In both the aforesaid embodiments the layer of cholesterol can practically be prepared or deposited by evaporation of a solution of cholesterol in a suitable organic solvent.

Finally, in a different embodiment of the invention, the intimate contact between water-insoluble cholesterol and water-soluble saponins can also be achieved in continuous flow microreactors where separate solutions of cholesterol and saponins are mixed at high speed and high turbulence.

The skilled artisan will appreciate that the term "reaction vessel" refers to any kind and size of container, test tube, barrel, flask, jug, bin or receptacle which is suitable for, and compatible with, the unit operations outlined in the process according to the first aspect. A reaction vessel can conveniently be selected from normal laboratory equipment such as test tubes, centrifuge tubes, one- or multi-necked round-bottomed or pear-shaped flasks etc, which are typically produced from glass or suitable, solvent resistant polymers. A reaction vessel for scale-up and production purposes can be selected from pilot-scale and production scale reactors, which can be glass-lined or produced from stainless steel or other alloys.

The skilled artisan will further appreciate that by the term "a water-insoluble, porous article" is meant any article of suitable size having an open cell structure and a suitable shape, such as a hollow fibre, and made from a suitable, water-insoluble porous material, such as porous glass, aerogels and other inorganic gels, porous alumina, zirconia or silica particles, metal foams and porous polymers.

The skilled artisan will further appreciate that the removal of solvent from the cholesterol solution conveniently can be performed by evaporation of the solution. This comprises applying a moderate vacuum, optionally with heating, whilst stirring the contents of the reaction vessel. Said stirring can be performed by spinning the reaction vessel or by applying an internal stirrer inside the reaction vessel such as a stirring bar or paddle stirrer.

Alternatively, the removal of solvent from the cholesterol solution can be carried out by passing a stream of air, argon or nitrogen into the reaction vessel, optionally whilst stirring the contents therein.

Regardless of the method whereby the solvent is removed, said removal effects a deposition of a layer of cholesterol having a varying thickness and roughness on the inside of the reaction vessel and/or the surface of the porous article.

Regarding point b) of the second aspect, NanoQuil F70 nanoparticles were produced using 4 different aqueous reaction media: Distilled water (D.W.), Saline solution (0.85% NaCl in D.W.), Acetate buffer (pH 4.6) and PBS (pH 7.4) according to the above NanoQuil F70 production protocol.

Differences in particle size (hydrodynamic diameter) were observed by DLS in these formulations: NanoQuil F70 formulated in PBS gives the biggest size (about 42 nm), followed by NanoQuil F70 formulated in Saline solution (about 35 nm). NanoQuil F70 particles formulated in Acetate buffer (pH 4.6) and distilled water give particle sizes of around 25 and 24 nm respectively (see FIG. 3C).

By DLS analysis, the diameter of particles which is given is the hydrodynamic diameter. The hydrodynamic diameter, or Stokes diameter, is the diameter of an equivalent hard sphere that diffuses at the same rate as the analyte, i.e. that of a sphere that has the same translational diffusion coefficient as the particle being measured, assuming a hydration layer surrounding the particle. What is therefore measured is the radius of gyration of the particles in solution. This does not give information about the morphology of the particle under "static" conditions; this can however be assessed by TEM.

Using TEM analysis, it was found that using different aqueous reaction media under point b) above also leads to other differences in particle morphology. As can be seen from the below table, the ratio of open vs. closed nanoparticles (Form A: Form B) produced in the different media is different. For PBS buffer the ratio is about 8:92 A: B, but for distilled water and acetate buffer the ratio is about 40:60. All values measured by TEM image analysis.

| NanoQuil F70 Sample | Circular Form A | Perimeter (nm) | Open ended Form B | Length (nm) |
|---|---|---|---|---|
| H₂O pH ~5.2 | 39.7% | 75.7 ± 7.4 (R = 12 nm) | 60.3% | 43.9 |
| NaCl 150 mM pH ~5.2 | | To be performed | | |
| Na-Acetate 10 mM pH 4.6 | 35.4% | 74.7 ± 7.3 (R = 11.9 nm) | 64.6% | 44.1 |
| PBS pH 7.4 | 8.3% | 103.5 ± 17.8 (R = 16.5 nm) | 91.7% | 61.1 |

The NanoQuil F70 particle morphology can thus be fine-tuned by changing the process parameters, which is a great advantage over prior art procedures. Applicants envisage that the various types of particles and composition ratios will find individual uses.

Thus, in one embodiment the aqueous reaction medium added under point b) is a buffer, such as an acetate or PBS buffer. In another embodiment the aqueous reaction medium added under point b) is a solution of one or more salts such as saline (0.85% NaCl in distilled water). In yet another embodiment the aqueous reaction medium added under point b) is salt-free distilled water. In a preferred embodiment the aqueous reaction medium added under point b) is an acetate buffer having a pH of ~4.6.

In another embodiment the manufacturing process for NanoQuil F70 particles is conducted at a pH of between 4-5. In another embodiment the manufacturing process for NanoQuil F70 particles is conducted at a pH of between 5-6. In another embodiment the manufacturing process for NanoQuil F70 particles is conducted at a pH of between 6-7. In another embodiment the manufacturing process for NanoQuil F70 particles is conducted at a pH of between 7-8.

Regarding point c) of the second aspect, addition of Quil A (or another quilaja fraction) is preferably performed using an aqueous solution of a concentration at around 1 mg/ml. Sufficient amounts of such a solution is added to produce a final ratio of 10:1 to 20:1, preferably a final ratio of 16:1 (w/w) saponins: Cholesterol.

Heating of the resulting reaction mixture at point d) of the process according to the second aspect is an essential feature of the present invention, which drastically changes the morphology and particle size distribution of the particles produced vis-à-vis the particles of WO2013051994, as described above.

Thus, in a preferred embodiment, the resulting reaction mixture at point d) of the process according to the first aspect is heated to 70° C.±5° C. for about an hour. The skilled artisan will appreciate that although heating is an essential feature of the present invention, the exact reaction temperature, period of heating, rate of heating and temperature profile during heating and subsequent cooling, especially when scaling the production method to a new scale, are parameters which all need to be analyzed and optimized. Analyzing and optimizing process parameters are tasks well understood by the skilled artisan, and considered routine tasks to perform, which do not require inventive skills.

Regarding point e) of the second aspect, the final isolation of the NanoQuil F70 particles of the invention includes a purification step. This step is included because the "raw" NanoQuil F70 particles, which result from the process of formulating saponins with cholesterol according to the second aspect of the present invention, are never totally free of residual free saponin micelles, and thus the NanoQuil F70 crude product may contain free saponin micelles in varying amounts from batch to batch. The final purification step reduces the batch-to-batch variability to an acceptable level, which will be discussed in the following.

Saponins from *Quillaja* species, such as QuilA—a commercial mixture of partially purified saponins from *Quillaja saponaria* Molina—have an inherent lytic activity on biological membranes when delivered as micelles in aqueous buffers, as many other saponins (Kensil, C. R. et al. (1991). Separation and characterization of saponins with adjuvant activity from *Quillaja saponaria* Molina cortex. The Journal of Immunology, 146 (2), 431-437; Oda, K., et al. (2000). Adjuvant and haemolytic activities of 47 saponins derived from medicinal and food plants. Biological Chemistry, 381 (1), 67-74). In this form, Quillaja saponins induce an adverse acute inflammation syndrome when injected as vaccine adjuvants, due to its potent cell-membrane lytic effect (a reaction that leads to the disruption or lysis of a cell).

The structure of the saponin molecules, possessing both hydrophilic and lipophilic moieties provides these molecules with a pronounced detergent effect.

Upon injection, the saponin molecules as such interact with cholesterol and phospholipids on cell membranes, thereby acting as a detergent. This effect is quantified in the hemolysis assay carried out on sheep red blood cells, as described in the Experimental section hereinbelow.

The solvent effect of the saponin leads to a lytic reaction with the tissue surrounding the inoculum. Dosage recommendations for using saponins as vaccine adjuvants therefore must reflect a balance of achieving a good immune-stimulating effect without also inducing clinically significant adverse reactions at the injection site (in the form of ulcers, necrosis etc.). This, however, confers some limitations for the dosage when applying these adjuvants.

When preparing the NanoQuil F-70, as well as other saponin-containing particulate adjuvants, there may be a certain excess of free saponin that is not immobilized by incorporation into, in this case, the NanoQuil F70 complex with cholesterol.

This free saponin will still possess the ability to induce lytic reactions in the surrounding tissue, as discussed hereinabove. For a saponin-based adjuvant to be accepted in vaccination, its membrane lytic potential needs to be as low as possible without affecting the immunopotentiating effect of the saponins. To this end, a purification step of the NanoQuil F70 nanoparticles is necessary to ensure an acceptable product.

Applicants have found that gel filtration (in the following referred to as size exclusion chromatography, SEC) satisfactorily removes excess saponins from the crude product. SEC methodology is moreover readily scalable to industrial production scale.

Gel filtration (also referred to as size exclusion chromatography, SEC) separates molecules according to differences in size as they pass through a gel filtration medium packed in a column. Unlike ion exchange or affinity chromatography, molecules do not bind to the chromatography medium so buffer composition does not directly affect resolution (the degree of separation between peaks). Consequently, a significant advantage of gel filtration is that conditions can be varied to suit the type of sample or the requirements for further purification, analysis or storage without altering the separation.

In one embodiment the removal of residual saponin is carried out using, for example, Sephacryl 300 or another gel filtration medium which the skilled artisan will be able to choose without inventive efforts. The SEC methodology is capable of separating the NanoQuil F70 particles with an average size of 20-50 nm (hydrodynamic diameter dependent on reaction medium) from the residual saponin micelles having an average size of ~5 nm and thereby obtain a product with a highly reduced lytic effect.

The effect of the removal of excess saponin on the hemolytic activity of the NanoQuil F70 nanoparticles is thoroughly documented in the Experimental section hereinbelow, and can be easily demonstrated by comparing the hemolytic effect of the "raw" nanoparticles with the SEC purified particles, see FIGS. 9 and 10.

The hemolytic effect of the analysed nanoQuil F70 nanoparticles (which contain complexed QuilA) is most efficiently presented as "QuilA equivalents". Compared with QuilA itself, unpurified (raw) nanoQuil F70 induces a hemolytic effect at an equivalent QuilA concentration of 1 mg/mL. At 2 mg/mL unpurified nanoQuil F70, the hemolytic effect is similar to that of 0.2 mg/ml free QuilA. The hemolytic effect of this preparation can be therefore deemed about 10× reduced vis-à-vis QuilA itself.

Sephacryl 300-HR purified nanoQuil F70 does not show any hemolytic effect until an equivalent QuilA concentration of 2 mg/ml. At 4 mg/ml, purified nanoQuil F70 displays a hemolytic effect which is lower or similar to that induced by 0.1 mg/mL free QuilA or 1 mg/ml unpurified nanoQuil F70. The hemolytic effect of the purified nanoQuil F70 nanoparticles can thus be deemed at least 40× reduced vis-à-vis QuilA itself, or about 4× reduced vis-à-vis the raw nanoQuil F70.

This effect (reduction of the lytic effect) of the SEC purification of the nanoQuil F70 particles is surprisingly high, and moreover very significant from a treatment perspective, as it raises the upper limit of how much saponin-containing adjuvant can safely be injected without concomitantly increasing the local reactogenicity. As a result, the use of nanoQuil F70 particles as adjuvant may render it possible to induce a higher immune response for a given injection.

In a preferred embodiment of the invention, the hemolytic effect induced by the saponin-containing nanoQuil F70 nanoparticles is reduced at least 20χ, such as 20χ, 30× or 40× as compared with the hemolytic effect induced by the same saponin, such as QuilA, in pure, uncomplexed form by means of gel filtration techniques such as size exclusion chromatography (SEC) performed on the raw, or crude nanoQuil F70 nanoparticles.

Comparing the method steps of the procedure as disclosed in WO2013051994 with that of the present invention, it is clear that the structural characteristics which define the nanoQuil F70 nanoparticles of the second aspect are a direct result of the modifications of the manufacturing procedure.

Accordingly, in a specific embodiment, the nanoparticles according to the first aspect of the invention are obtainable by the method according to the second aspect.

Apart from their usage as vaccine adjuvants, the nanoQuil F70 nanoparticles according to the invention may also be used as delivery systems for one or several compounds e.g. for pharmaceuticals including those used for treatment of cancer and nutrition related compounds where the additional substance(s) provide additional functions and complementary modes of action.

In a third aspect the NanoQuil F70 nanoparticles and compositions comprising them may be used as such as a pharmaceutical, optionally in a pharmaceutical composition further comprising pharmaceutically acceptable buffers, diluents excipients, additives, adjuvants and/or carriers.

Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in Remington's Pharmaceutical Sciences, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

The invention also comprises a pharmaceutical composition further comprising at least one pharmaceutically active compound, such as anticancer drugs, platinum coordination compounds, taxane compounds, camptothecin compounds, anti-tumour *vinca* alkaloids, anti-tumour nucleoside derivatives, nitrogen mustard or nitrosourea alkylating agents, anti-tumour anthracycline derivatives, trastzumab and anti-tumour podophyllotoxin derivatives, Quillaja *saponaria* Molina and sub fragments thereof, receptors for antibodies or monoclonal antibodies such as Fc receptors or the DD of Protein A of *Staphylococcus aureus*, agents for treating cancer, such as agents selected from the group consisting of Cytarabin, Daunorubicin, Paclitaxel, Docetaxel, Cabazi-taxel, Toricsel and Trabectidin, which active compound may be integrated into the nanoparticle or mixed with the composition.

The further anti-cancer agents are preferably selected from platinum coordination compounds, taxane compounds, camptothecin compounds, anti-tumour *vinca* alkaloids, anti-tumour nucleoside derivatives, nitrogen mustard or nitrosourea alkylating agents, anti-tumour anthracycline derivatives, trastzumab and anti-tumour podophyllotoxin derivatives.

The term "platinum coordination compound" is used herein to denote any tumour cell growth inhibiting platinum coordination compound which provides platinum in the form of an ion. Preferred platinum coordination compounds include cisplatin, carboplatin, chloro(diethylenetriamine)-platinum (II) chloride; dichloro(ethylenediamine)-platinum (II); diamine (1, 1-cyclobutanedicarboxylato)-platinum (II) (carboplatin); spiroplatin; iproplatin; diamine (2-ethylmalonato)-platinum (II); (1,2-diaminocyclohexane) malonato-platinum (II); (4-carboxyphthalo-1,2-diaminocyclohexane) platinum (II); (1,2-diaminocyclohexane)-(isocitrato) platinum (II); (1,2-diaminocyclohexane)-cis-(pyruvato) platinum (II); (1,2-diaminocyclohexane)oxalato-platinum (II); ormaplatin and tetraplatin.

Cisplatin is commercially available for example under the trade name Platinol from Bristol Myers Squibb Corporation as a powder for constitution with water, sterile saline or other suitable vehicle. Other platinum coordination compounds and their pharmaceutical compositions are commercially available and/or can be prepared by conventional techniques.

Taxane compounds include for example Taxol from Bristol Myers Squibb, docetaxel (Taxotere) from Rhone-Poulenc Rorer and Carbazitaxel from Sanofi Pasteur. Other taxane compounds may be prepared in conventional manner for example as described in EP 253738, EP 253739 and WO 92/09589 or by processes analogous thereto.

Camptothecin compounds include irinotecan and topotecan. Irinotecan is commercially available for example from Rhone-Poulenc Rorer under the trade name Campto and may be prepared for example as described in European patent specification No. 137145 or by processes analogous thereto. Topotecan is commercially available for example from SmithKline Beecham under the trade name Hycamtin and may be prepared for example as described in European patent specification No. 321122 or by processes analogous thereto. Other camptothecin compounds may be prepared in conventional manner for example by processes analogous to those described above for irinotecan and topotecan.

Anti-tumour *vinca* alkaloids include vinblastine, vincristine and vinorelbine referred to above. Vinblastine is commercially available for example as the sulphate salt for injection from Eli Lilly and Co under the trade name Velban, and may be prepared for example as described in German patent specification No. 2124023 or by processes analogous thereto. Vincristine is commercially available for example as the sulphate salt for injection from Eli Lilly and Co under the trade name Oncovin and may be prepared for example as described in the above German patent specification No. 2124023 or by processes analogous thereto. Vinorelbine is commercially available for example as the tartrate salt for injection from Glaxo Wellcome under the trade name Navelbine and may be prepared for example as described in U. S. patent specification No. 4307100, or by processes analogous thereto. Other anti-tumour *vinca* alkaloids may be prepared in conventional manner for example by processes analogous to those described above for vinoblastine, vincristine and vinorelbine.

Anti-tumour nucleoside derivatives include 5-fluorouracil, gemcitabine and capecitabine referred to above. 5-Fluorouracil is widely available commercially, and may be prepared for example as described in U.S. Pat. No. 2,802,005. Gemcitabine is commercially available for example from Eli Lilly under the trade name Gemzar and may be prepared for example as described in European patent specification No. 122707 or by processes analogous thereto.

Capecitabine is commercially available for example from Hoffman-La Roche under the trade name Xeloda and may be prepared for example as described in European patent specification No. 698611 or by processes analogous thereto. Other anti-tumour nucleoside derivatives may be prepared in conventional manner for example by processes analogous to those described above for capecitabine and gemcitabine.

Nitrogen mustard compounds include cyclophosphamide and chlorambucil. Cyclophosphamide is commercially available for example from Bristol-Myers Squibb under the trade name Cytoxan and may be prepared for example as described in U. K. patent specification No. 1235022 or by processes analogous thereto. Chlorambucil is commercially available for example from Glaxo Welcome under the trade name Leukeran and may be prepared for example as described in U. S. patent specification No. 3046301, or by processes analogous thereto. Preferred nitrosourea compounds for use in accordance with the invention include carmustine and lomustine referred to above. Carmustine is commercially available for example from Bristol-Myers Squibb under the trade name BiCNU and may be prepared for example as described in European patent specification No. 902015, or by processes analogous thereto. Lomustine is commercially available for example from Bristol-Myers Squibb under the trade name CeeNU and may be prepared for example as described in U. S. patent specification No. 4377687, or by processes analogous thereto.

Anti-tumour anthracycline derivatives include daunorubicin, doxorubicin and idarubicin referred to above. Daunorubicin is commercially available for example as the hydrochloride salt from Bedford Laboratories under the trade name Cerubidine, and may be prepared for example as described in U. S. patent specification No. 4020270, or by processes analogous thereto.

Doxorubicin is commercially available for example as the hydrochloride salt from Astra, and may be prepared for example as described in U. S. patent specification No. 3803124 or by processes analogous thereto. Idarubicin is commercially available for example as the hydrochloride salt from Pharmacia & Upjohn under the trade name Idamycin, and may be prepared for example as described in U. S patent specification No. 4046878 or by processes analogous thereto Other anti-tumour anthracycline derivatives may be prepared in conventional manner for example by processes analogous to those described above for daunorubicin, doxorubicin and idarubicin.

Trastzumab is commercially available from Genentech under the trade name Herceptin and may be obtained as described in U. S. Patent specification No. 5821337 or PCT patent specifications WO 94/04679 and WO 92/22653.

Anti-tumour anti-tumour podophyllotoxin derivatives include etoposide and teniposide. Etoposide is commercially available for example from Bristol-Myers Squibb under the trade name VePesid, and may be prepared for example as described in European patent specification No. 111058, or by processes analogous thereto. Teniposide is commercially available for example from Bristol-Myers Squibb under the trade name Vumon and may be prepared for example as described in PCT patent specification No. WO 93/02094, or by processes analogous thereto. Other anti-tumour podophyllotoxin derivatives may be prepared in conventional manner for example by processes analogous to those described above for etoposide and teniposide.

Thus, anticancer drugs may e.g. be chosen from:

1. Polyfunctional alkylating agents:
  Nitrosoureas, Mustards (Nitrogen Mustards), Methanesulphonates (Busulphan), Ethylenimines
2. Other Alkylating Drugs:
  Procarbazine (Matulane), Dacarbazine (DTIC), Altretamine (Hexalen), Cisplatin (Platinol)
3. Antimetabolites:
  Antifolic acid compounds (Methotrexate), Amino acid Antagonists (Azaserine)
4. Purine antagonists:
  Mercaptopurine (6-MP),Thioguanine (6-TG), Fludarabine Phosphate, Cladribine (Leustatin), Pentostatin (Nipent)
5. Pyrimidine antagonists:
  Fluorouracil (5-FU), Cytarabine (ARA-C), Azacitidine
6. Plant alkaloids:
  Vinblastine (Velban), Vincristine (Oncovin), Etoposide (VP-16,VePe-sid),Teniposide (Vumon), Topotecan (Hycamtin), Irinotecan (Camptosar), Paclitaxel (Taxol), Docetaxel (Taxotere)

7. Antibiotics:
Anthracyclines, Doxorubicin (Adriamycin, Rubex, Doxil), Daunorubicin (DaunoXome), Dactinomycin (Cosmegen), Idarubincin (Idamycin), Plicamycin (Mithramycin), Mitomycin (Mutamycin), Bleomycin (Blenoxane)
8. Monoclonal Antibodies,
9. Hormonal agents:
Tamoxifen (Nolvadex), Flutamide (Eulexin), Gonadotropin-Releasing Hormone Agonists, (Leuprolide and Goserelin (Zoladex)), Aromatase Inhibitors, Aminoglutethimide, Anastrozole (Arimidex),
10. Miscellaneous anticancer drugs:
Amsacrine, Hydroxyurea (Hydrea), Asparaginase (Elspar), Mitoxantrone (Novantrone), Mitotane, Retinoic Acid Derivatives, Bone Marrow Growth Factors, Amifostine.

Amphipathic and hydrophobic molecules, which may be selected from an antigen, an adjuvant, a targeting molecule, a pharmaceutical compound and a nutriment may be integrated into the nanoQuil F70 nanoparticles according to the present invention, or mixed therewith in a composition. A composition according to the present invention may also contain different amphipathic and hydrophobic molecules incorporated into separate nanoparticles.

The pharmaceutical composition comprising the NanoQuil F70 nanoparticles of the present invention may as mentioned above be used as a vaccine adjuvant, e.g. for use in combination with a vaccine under development, or already implemented in licensed vaccines, for use in combination with a seasonal influenza virus vaccine, for use in combination with a pandemic influenza vaccine or for use in combination with an emergency vaccine, such as a vaccine against a biological weapon, or for use as a component in a drug delivery system. The NanoQuil F70 nanoparticles of the present invention are thus useful as adjuvants in vaccines both for human and veterinary use.

Thus, the invention also regards a pharmaceutical vaccine formulation, such as a human or veterinary vaccine, comprising the NanoQuil F70 particles according to the present invention, and especially as an adjuvant as mentioned above.

In a preferred embodiment, NanoQuil F70 particles which comprise QS-21 saponin are particularly suited to be used as adjuvants in human vaccines. In another embodiment, NanoQuil F70 particles which comprise QuilA saponin are particularly suited to be used as adjuvants in veterinary vaccines.

In another embodiment, the pharmaceutical composition further comprises diterpenes, such as one or more steviol glycosides.

The invention also relates to a method for treating or preventing a disease caused or complicated by an organism, comprising administering to a subject a pharmaceutical vaccine formulation according to the invention to a person in need thereof.

Further, the invention regards a method for treatment of cancer, comprising administering to a patient in need thereof a pharmaceutically effective amount of nanoparticles or a composition according to the invention. According to one embodiment the said cancer is leukemia, lymphom, myelom, breast cancer, prostata cancer, renal cancer, pancreas cancer, ovarie cancer, brain cancer, cervix cancer, lung, cancer, liver, cancer, kidney cancel, oral cancer, blood cancer. The cancer may be situated in Adrenal gland (Adrenal Gland Cancer, Adenocarcinoma of the Adrenal Gland, Adrenocorticol Carcinoma; Anus, Anal Cancer (Squamous Cell Carcinoma of the Anus); Bladder Cancer (Squamous Cell Carcinoma of the Bladder), Bladder Cancer (Transitional cell carcinoma of the Bladder); Blood, Disseminated Intravascular Coagulation, Hyponatraemia, Neutropaenic sepsis, Tumour Lysis Syndrome; Bone, Endochondroma (chondroma, Ollier's disease), Ewings Sarcoma, Osteosarcoma, (Osteogenic sarcoma), Metastases to the Bone, Bone Cancer (Chondrosarcoma of Cartilage); Bone Marrow, Chronic Myeloid Leukaemia, Multiple Myeloma, Promyelocytic Leukaemia (PML), Myelodysplastic syndrome (MDS), Chronic Lymphocytic Leukaemia, Acute Lymphoblastic Leukaemia (ALL), Acute Myeloid Leukaemia (AML); Brain, Brain Cancer (Glioblastoma Multiforme of the Brain), Brain tumour (Glioma of the Brain), Lymphoma of the Brain, Medulloblastoma/Primitive Neuroectodermal tumour (PNET) [Medulloblastoma/Primitive Neuroectodermal tumour (PNET)], Meningioma of the Brain, Neuroblastoma, Primitive neuroectodermal tumour of the brain (PNET), Brain Metastasis, Acoustic Neuroma, Brain Tumour (Astrocytoma of the Brain); Breast, Breast Cancer (Carcinoma of the Breast), Breast Cancer (Inflammatory Carcinoma of the Breast), Male Breast Cancer (Male Breast Carcinoma), Breast Cancer (Invasive Breast Carcinoma) [Invasive Breast Carcinoma (Breast Cancer)], Breast Cancer (Pre-Invasive Lobular Carcinoma; Lobular Carcinoma In Situ; LCIS) [Pre-Invasive Lobular Carcinoma (Lobular Carcinoma In Situ; LCIS; Breast Cancer)], Breast Cancer (Pre-Invasive Ductal Carcinoma; Ductal Carcinoma In Situ; DCIS) [Pre-Invasive Ductal Carcinoma (Ductal Carcinoma In Situ; DCIS; Breast Cancer)]; Caecum, Bowel Cancer (Adenocarcinoma of the Caecum); Cervix, Cervical Cancer (Squamous Cell Carcinoma of the Cervix); Colorectal, Colon Cancer (Adenocarcinoma of the Colon), Rectal Cancer (Adenocarcinoma of the Rectum) 1, Head and Neck, Tonsil Cancer (Lymphoma of the Tonsil), Cancer of the larynx (Laryngeal cancer, Squamous Cell Carcinoma of the Larynx), Pharynx Cancer (Squamous Cell Carcinoma of the Pharynx), Tongue Cancer (Squamous Cell Carcinoma of the Tongue), Throat cancer (Squamous Cell Carcinoma of the Tonsil), Oral Cancer (Squamous Cell Carcinoma of the Floor of the Mouth); Kidney, Kidney Cancer (Renal Cell Carcinoma; RCC); Liver, Liver Cancer (Hepatocellular Carcinoma), Metastases to the Liver; Lung, Lung Cancer (Large Cell Carcinoma of the Lung), Pleural effusion, Lung Cancer (Adenocarcinoma of the Lung), Small Cell Lung Cancer (Carcinoma of the Lung), Non-Small Cell Lung Cancer (NSCLC), Malignant Mesothelioma of the Pleura, Lung Cancer (Squamous Cell Carcinoma of the Lung); Lymphatic System; Hodgkin's lymphoma, Hodgkin's Lymphoma; non-Hodgkin's lymphoma, Burkitt's lymphoma, Cerebral Lymphoma, Cutaneous T cell Lymphoma, Follicular lymphoma, Lymphoblastic lymphoma (non-Hodgkin's lymphoma), MALT lymphoma, Mantle cell lymphoma, Mediastinal (thymic) large B cell lymphoma, Nodal Marginal Zone B cell Lymphoma, Non-Hodgkin's Lymphoma, Peripheral T cell lymphoma, Small lymphocytic lymphoma, Diffuse large B cell lymphoma (DLBCL), Anaplastic Large Cell Lymphoma (ALCL); Muscle, Cancer of the Bile Duct (Cholangiocarcinoma Biliary Cancer), Leiomyosarcoma of Muscle, Rhabdomyosarcoma of Muscle, Soft tissue Sarcomas; Oesophagus, Oesophageal Cancer (Squamous Cell Carcinoma of the Oesophagus), Oesophageal Cancer (Adenocarcinoma of the Oesophagus); Ovary, Ovarian Cancer (Adenocarcinoma of the Ovary); Pancreas, Pancreatic Cancer (Adenocarcinoma of the Pancreas), Pancreatic Neuroendocrine Tumour (PNET); Penis, Cancer of the Penis (Squamous Cell Carcinoma of the Penis), Peyronie's Disease; Pituitary gland, Pituitary Gland Cancer (Carcinoma of the Pituitary gland), Syndrome of inappropriate antidiuretic hormone secretion (SIADH) [Syndrome of inappropriate antidiuretic hormone secretion (SIADH)]; Prostate, Prostate Cancer (Neuroendocrine Carcinoma of the Prostate), Prostate Cancer (Adenocarcinoma of the Prostate); Skin, Skin Cancer (Basal Cell Carcinoma of the Skin), Skin Cancer (Squamous Cell Carcinoma of the Skin), Merkel Cell Carcinoma (MCC), Skin Cancer (Malignant Skin Melanoma), Moles (Benign Pigmented Lesions, Benign Melanocytic Lesions, Melanocytic Naevi, Nevocytic Naevi); Small Intestine, Small Intestine Cancer (Lymphoma of the Small Intestine), Small Bowel Cancer (Adenocarcinoma of the Small Intestine); Spinal Cord, Glioma of the Spinal Cord, Meningioma of the Spinal Cord, Metastases of the Spinal Cord, Spinal Cord Astrocytoma (Tumour), Spinal Cord Cancer (Lymphoma of the Spinal Cord); Stomach, Zollinger-Ellison Syndrome (Gastrinoma), Lymphoma of the Stomach (Gastric Lymphoma), Stomach Cancer (Adenocarcinoma of the Stomach); Testicle, Testicular Cancer (Seminoma of the Testicle), Testicular Cancer (Teratoma of the Testicle); Thyroid, Thyroid Cancer (Follicular Cell of the Thyroid), Medullary Cell of the Thyroid, Papillary Cell of the Thyroid, Thyroid Cancer (Anaplastic of the Thyroid); Uterus, Gestational Trophoblastic Disease (Molar Pregnancy) [Molar Pregnancy (Gestational Trophoblastic Disease, GTD)], Uterine Cancer (Adenocarcinoma of the Endometrium); Vulva, Vulval Cancer (Squamous Cell Carcinoma of the Vulva); Other cancers, Tumour of unknown primary (TUP), Chronic Pain Syndrome, Carcinoid Tumour and Carcinoid Syndrome, Neuroendocrine Tumour; Other Cancer diseases, Anaemia of Chronic Disease, Cancer Pain, Failed Back Surgery Syndrome (FBSS), HIV AIDS (Human Immune Deficiency Virus & Acquired Immune Deficiency Syndrome), Kidney Disease-Chronic Renal Failure, Malnutrition, Ototoxicity, Petechiae skin purpura, Prostatic Intraepithelial Neoplasia (PIN).

Examples of the effect of nanoQuil F70 nanoparticles on cancer cells are given in the Examples section hereinbelow.

The pharmaceutical compositions may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The solutions or suspensions may also comprise at least one of the following adjuvants: sterile diluents such as water for injection, saline, fixed oils, polyethylene glycols, glycerol, propylene glycol or other synthetic solvents, antibacterial agents such as benzyl alcohol or methyl paraben, antioxidants such as ascorbic acid or sodium bisulfite, chelating agents such as ethylene diamine tetraacetic acid, buffers such as acetates, citrates or phosphates, and agents for adjustment of the tonicity such as sodium chloride or dextrose. The parenteral preparation may be enclosed in ampoules, disposable syringes or multiple dosage vessels made of glass or plastic.

Generally, the NanoQuil F70 particles of the invention are administered in a pharmaceutically effective amount. The amount of the particles actually administered will be typically determined by a physician, in the light of the relevant circumstances, including the condition to be treated, the chosen route of administration, the actual compound administered, the age, weight, and response of the individual patient, the severity of the patient's symptoms, and the like.

The nanoparticle according to the invention may be used as an adjuvant in any vaccine against any microorganisms. It may be used on any animal such as birds, mammals such as humans, domestic animals such as cats, dogs, sheep, goat, pigs, cattle and horses. According to one embodiment the invention is used as adjuvant in a vaccine against streptococci in animals and influenza in horses.

Examples of the effect of nanoQuil F70 nanoparticles as a vaccine adjuvant are given in the Examples section hereinbelow.

Doses for both human and veterinary use may vary according to other compounds included. In view of duration of treatment the dose may range from <50 µg to 1 mg or more per day.

Examples

Example 1-Production of Raw NanoQuil F70 Nanoparticles Using PBS or Acetate Buffer as Reaction Medium Materials
Plant cholesterol. Lot. SCOL 129-2. Material code: C1231, Sigma-Aldrich.
Quil A stock 100 mg/mL, Brenntag Biosector A/S.
PBS buffer pH7.4, or Acetate 2-10 mM buffer pH 4.6.
Distilled water.
Saline solution (0.85% NaCl in distilled water).
Acetone, Ph. Eur. ≥99.5%.
50 mL Cellstar tubes
Air pump. Eheim 200, type 3702010.
Thermoshaker and block thermostats with smart control. MKR13 from Hettich Lab Technology, The Netherlands.
Sorvall ST16R centrifuge, Thermo Scientific.
LaminAir flow hood, Holten. Thermo Fisher Scientific.
Vacuum filtration, 1000 mL, SFCA, 0.22 µM sterilized, VWR European article No 514-1058.
Pipettes and tips (sterilized).

Procedure
1. Weigh plant-derived cholesterol 3.125 mg/tube×5 tubes=15.625 mg.
2. Add 5 mL acetone to the cholesterol, dissolve well using Vortex
3. Dispend the cholesterol solution into 1 mL/tube.
4. Evaporate acetone via pumping air into the tube while rotating the tube in order to deposit the cholesterol evenly on the V-bottom of the test tube.
5. Add 70° C. warm aqueous reaction medium (50 mL per tube): distilled water, saline solution (0.85% NaCl), acetate buffer (pH 4.6) or PBS buffer (pH 7.4).
6. Add 500 µl/tube of 100 mg/ml Quil A stock to give 1 mg/ml Quil A solution.
7. Incubate at 70° C. for 60 min on MKR13 (see Materials).
8. Cool down at 4° C. directly.
9. Store at 4° C. overnight.
10. Centrifuge at 4696×G for 45 min.
11. Filtration of the pooled supernatant through a 0.22 µM filter.

Example 2-Reproducibility Testing

In order to evaluate reproducibility of the procedure outlined in Example 1 hereinabove, NanoQuil F70 nanoparticles were produced three times in three successive days on 18, 19 and 20 Jul. 2018. These three batches (Test-1, -2 and -3) of NanoQuil F70 were formulated in 5-50 mL Falcon tubes per batch (250 mL) and incubated for 1 hour at 70° C. as implicated by the name NanoQuil F70 (formulation at 70° C.). As a non-limiting example, the formulation protocol can be simplified as follows:

Weigh 15.625 mg plant cholesterol.
Add 5 mL acetone to the cholesterol, dissolve well.
Dispense the cholesterol solution 1 mL/tube into 5-50 mL Falcon tubes.
Evaporate acetone by pumping air into the tube while rotating the tube in order to deposit the cholesterol evenly on the V-bottom of each tube.
Add 70° C. PBS, 50 mL/tube.
Add 500 µl/tube 100 mg/ml Quil A stock to give 1 mg/ml Quil A solution.
Incubate at 70° C. for 60 min.
Cool down at 4° C. directly.
Store at 4° C. overnight.
Centrifuge at 4696×g for 45 min.
Filtration of the pooled supernatant through 0.22 µM filter.
Store at 4° C.

Results and Discussions

1. Quil a Recovery in the Products

Quil A content of the produced NanoQuil F70 nanoparticles was measured using the Orcinol test (also known as Bial's test). The results are shown graphically in FIG. 12.

For the three test batches, Quil A recovery rates were high, 91.5%, 93.8% and 98.3% respectively, i.e. all above 90%.

2. Particle Size

The mean particle sizes of the three formulations were 46.32±1.48 nm, 40.07±0.98 nm and 42.20±0.74 nm, respectively, measured by Dynamic Light Scattering (DLS) analysis, see FIG. 5. FIG. 13 shows a graphic summary of the DLS measurements.

3. Reduction of Hemolysis Effect

The hemolysis reduction rates for the three batches are rather similar: 31% for Test-1, 29% for Test-2 and 31% for Test-3 (see the bar chart in FIG. 14). This can be viewed as similar levels of side effect reduction by formulating Quil A into F70 were achieved, i.e. high degree of reproducibility in side effect reduction. It is observed, however, that all test batches induce hemolysis to a degree which is unacceptably high for a vaccine adjuvant.

4. NanoQuil F70 Nanoparticles Produced in Other Reaction Media

NanoQuil F70 nanoparticles were produced using 4 different solvents: distilled water (D.W.), Saline solution (0.85% NaCl in D.W.), Acetate buffer (pH 4.6) and PBS (pH 7.4) according to the NanoQuil F70 protocol. Differences in particle size (hydrodynamic diameter) were observed by DLS in these formulations: NanoQuil F70 formulated in PBS gives the biggest size (about 42 nm), followed by NanoQuil F70 formulated in Saline solution (about 35 nm). NanoQuil F70 particles formulated in Acetate buffer (pH 4.6) and distilled water give particle sizes of around 25 and 24 nm respectively (see bar chart in FIG. 15).

Example 3-Size Separation of Raw NanoQuil F70 Particles with Sephacryl S300-HR Chromatography In order to remove free (non incorporated) saponins susceptible to increase cell lysis from the NanoQuil F70 particles, the crude NanoQuil F70 product is purified by Size Exclusion Chromatography (SEC).

A volume of 13 mL of Sephacryl S300-HR (GE Healthcare Life Sciences) was placed in a PD-10 cartridge and equilibrated with PBS buffer or acetate buffer. A volume of 1 mL of raw NanoQuil F70 particles as produced according to Example 1 hereinabove, was loaded on top of the column and allowed to percolate by gravity through the Sephacryl material. Fractions of 1 mL were collected to be analyzed for saponins and cholesterol contents using RP-HPLC, as well as to be tested for hemolytic activity.

RP-HPLC of nanoQuil F70 SEC fractions

HPLC was used as a means to detect and quantify saponins and cholesterol in the S300-HR fractions. Total saponin and cholesterol contents are expressed as signal integrals from the HPLC Charged Aerosol Detector (CAD) and plotted as a function of the S300-HR elution volume. As with the Nile Red fluorescence detection method (see below), the S300-HR chromatogram shows two peaks of saponins centered at 6-7 mL and 9-10 mL, and cholesterol is mostly associated with the peak at 6-7 mL, as expected with NanoQuil particles.

Method:

100 µL of each S300HR fraction from NanoQuil F70 SEC fractionation was analysed on Kromasil C4 column using short chromatogram. The bar chart in FIG. 16 shows the integrated CAD signal for S300HR fractions corresponding to the sum of saponins peaks and the cholesterol peak.

Nile Red Fluorescence Analysis

Analysis of the S300-HR SEC fractions (45 µl of fraction+5 µL NileRed @10 UM for Fluorescence readings) with the fluorophore Nile Red shows the distribution of saponins, see the barchart in FIG. 17. Nile Red (NR) fluorescence is quenched by polar molecules such as water, and therefore shows only weak fluorescence in aqueous environment. However, when Nile Red interacts with apolar molecules such as the triterpenoid core of saponins, or gets incorporated into micellar structures, its fluorescence is enhanced by orders of magnitude. Nile Red is used as a tracer to monitor the presence of free QuilA saponins or NanoQuil particles in the S300-HR fractions.

The S300-HR chromatogram shows two peaks centered at fraction 6 mL, corresponding to NanoQuil particles (confirmed with TEM), and at 9 mL, corresponding to QuilA micelles.

NR fluorescence spectra for fractions 6 & 7 mL (not shown) displayed the typical blue shift for nanoQuil (which indicates interaction with cholesterol) with emission maximum at 570 nm, whereas fractions 9 & 10 mL displayed the typical spectrum for QuilA micelles with an emission maximum at 620 nm.

Hemolytic Assay of the NanoQuil F70 SEC Fractions

A volume of 120 µL of each fraction from the NanoQuil F70 SEC fractionation is added to 480 µL of diluted fresh sheep blood treated with anticoagulant. The dilution factor of NanoQuil F70 SEC fractions is 5-fold, whereas the sheep blood is diluted 12.5-fold in PBS buffer with EDTA 2 mM.

After incubation 45 min at 37° C., cells are sedimented by centrifugation and the amount of hemoglobin released in the supernatant is measured by Absorbance at 415 and 540 nm. Hemolytic activity is expressed as a function of the Absorbance value at 540 nm and against a calibration range with QuilA saponin from 0.4 mg/ml to 1.0 mg/mL. The results are shown in FIG. 18.

The most hemolytic S300-HR fractions, i.e. 9 mL and 10 mL, are those containing free QuilA. Fractions 6 mL and 7 mL containing nanoQuil F70 do not show hemolytic effect in the conditions of the assay.

This can also be expressed in "equivalents QuilA", see the barchart in FIG. 19.

The raw nanoQuil F70 product on the other hand, does show hemolytic effect from 1 mg/ml equivalent QuilA and up. The results are shown in FIG. 20.

Results

A typical RP-HPLC chromatogram used for the quantitative analysis of the NanoQuil F70 nanoparticles is shown on FIG. 6. For a fixed amount of QuilA saponin at 1 mg/mL, spiking with cholesterol from 0.1 mg/ml to 0.8 mg/ml yielded a linear response over this concentration range, which could be used for calibration and estimations of cholesterol contents in unknown fractions (SEC fractions of NanoQuil F70).

The fraction eluting at 6 mL from the 13 mL Sephacryl S300-HR cartridge and containing purified NanoQuil F70 was analyzed by HPLC. Integration of the signal between 20 ml and 32 mL (indicated by a horizontal grey bar in FIG. 6) was used to quantify the saponins in the fraction. Integration of the signal at 39 mL was used to quantify cholesterol.

After SEC fractionation of NanoQuil F70 and quantitative analysis by RP-HPLC, FIG. 7 clearly shows that NanoQuil F70 particles are eluted first, in fractions 5 mL to 8 mL where both QuilA saponin and cholesterol are found, whereas residual QuilA saponin with no cholesterol is eluted in later fractions from 9 mL to 12 mL. This result is consistent with the way SEC fractionation is supposed to work, where the larger the particles the less they permeate into the polymeric mesh of the Sephacryl beads; therefore the earlier they elute from the column. Nanoquil F70 particles have a hydrodynamic diameter of 20-50 nm (depending on reaction medium) whereas QuilA saponin micelles have a diameter of about 5 nm. The separation of NanoQuil particles and QuilA saponin micelles is also consistent with the fractionation range for Sephacryl S300-HR. A control experiment where only QuilA saponin was loaded onto the SEC column showed that QuilA saponin elutes in fractions 8-11 mL under the same conditions. This confirms that QuilA saponin found in fractions 5-8 mL, when NanoQuil F70 is injected (FIG. 7), is indeed associated with cholesterol. TEM pictures of the material in fractions 5-8 mL confirmed the identity of NanoQuil F70 particles. The SEC fractionation also shows that the amount of free QuilA saponin micelles (with no detectable cholesterol), in this batch, represents about 50% of the total amount of QuilA saponin in the raw NanoQuil F70 product. Finally, the initial ratio cholesterol/QuilA saponin measured in the raw NanoQuil F70 product was 3%, whereas it was found to be 13% in the combined SEC fractions from 5 ml to 8 mL.

A volume of 1 mL of NanoQuil F70 at 4.2 mg/mL QuilA was loaded onto the Sephacryl S300-HR column and 1 mL fractions were collected for HPLC quantitative analyses. SEC fractions containing detectable amounts of QuilA, from 4 mL to 13 mL are shown. NanoQuil F70 and QuilA are shown as references.

The hemolytic activity of each SEC fraction was measured and compared with a QuilA saponin reference at 1 mg/ml as well as NanoQuil F70 raw product at 1 mg/ml QuilA. The hemolytic activity of the different samples is presented as an Absorbance value at 540 nm which is directly correlated to the amount of hemoglobin released in the extracellular medium. FIG. 8 clearly shows that hemolytic activity was only observed for the SEC fractions 9-11 mL, where free QuilA micelles are essentially found. No hemolytic activity was recorded in fractions 5-8 mL, where purified NanoQuil was eluted (see FIG. 7 for reference). This confirms the identity of the material eluted in the SEC fractions, as it is known that free QuilA saponin micelles have a marked hemolytic activity, as exemplified by the QuilA reference at 1 mg/mL on FIG. 8. The results also show that purified NanoQuil F70 in fraction 6 mL, containing about 12% cholesterol/QuilA (w/w) do not show significant hemolytic activity (FIG. 8), therefore proving that direct incorporation of cholesterol into QuilA saponin micelles, using the protocol according to the present disclosure, and which leads to NanoQuil F70, also leads to a strong inhibition of the hemolytic effect of QuilA saponins.

Conclusion

Size exclusion chromatography using Sephacryl S300-HR beads was proven successful in separating NanoQuil F70 particles from residual free QuilA saponin micelles. Quantitative analysis of the SEC fractions by RP-HPLC and UV-Absorbance detection allowed for the determination of cholesterol/QuilA saponin ratios, and to confirm the identity of the material in each fraction (NanoQuil F70 or free QuilA saponin). The fractions containing free QuilA saponin showed a marked hemolytic effect whereas those containing purified NanoQuil F70 did not show any hemolytic effect. Last, it was shown that even the raw NanoQuil F70 sample containing about 50% of QuilA saponin as free residual saponin micelles presented only a limited hemolytic activity, compared to free QuilA in similar amounts. This confirms the validity of formulating QuilA saponin with cholesterol, directly, using the protocol in the present invention, in order to reduce significantly the inherent cell membrane lytic activity of QuilA saponins.

Example 4-Adjuvantic Effect of NanoQuil F70

The aim of the study was to compare the vaccine adjuvant effect of the Nanoquil F-70 particles with the G3 particles described in WO2013051994 and WO2014163558.

Study Outline:
  Antigen: Antigen x, 10 µg/immunization
  Adjuvans: G3-VAX (Adjuvaq-V100, #150609) or Nanoquil (#70, 180326), 5 µg/immunization
  Animals: Female BALB/c mice, 8/group
  Immunizations: A total of 3 s.c. immunizations, once every 4th week
  Samples: Serum collected 2 weeks post last immunization
  Analysis: ELISA (Goat-Anti-Mouse IgG/serum/TWIN-antigen/ST-HRP/TM)
  Results are shown graphically in FIG. 11.

Conclusion
  No significant difference was found between G3-VAX and Nanoquil.
  However, Nanoquil F-70 seems to generate slightly more potent ab responses and less variation than G3

Example 5-Apoptotic Effect of NanoQuil F70 on U937-1 Cancer Cells

Aim of the Experiment

The aim of this experiment is to explore the apoptotic effect of NanoQuil F70 on cancer cell line U937-1. U937 cells are a model cell line originally isolated from the histiocytic lymphoma of a male patient and is characterized as a human acute myeloid leukemia (AML) cell line.

EQUIPMENT

Sterile laminar flow hood, Biowizard Golden Line Ergosilence, Kojair
Vortex, IKA MS3 basic
Incubator, Forma Steri-Cycle CO2 incubators, TermoFisher Scientific
Refrigerator
Centrifuge; Allergra X-22R, Beckman Coulter
Microscope
Bürker chamber
Spectrophotometer (Labsystems Multiskan RC, type 351)

MATERIAL

NanoQuil F70 particles as obtained by the methods described hereinabove
U937-1 cells were kindly provided by Prof. Kenneth Nilsson (Rudbeck laboratory, Uppsala University, Uppsala, Sweden)
RPMI 1640 (product code: 992605; batch 16-8082; SVA, Uppsala) containing fetal bovine serum (Sigma Aldrich) at a final concentration of 10%, PeSt (60 µg/ml Penicillin; 50 µg/ml Streptomycin (Cat.No. 992450, SVA, Uppsala) and 2 mM L-Glutamine (Cat.No. 992005, SVA, Uppsala)
Cell culture plates, 96 well. Product code: 83.3924.500, Lot: 4025001, SARSTEDT
Phosphate buffer saline (PBS) pH 5,9-6.0 from substrate department, Uppsala University Hospital.
AlamarBlue® cell viability reagent 10×, ready-to-use solution
Distilled $H_2O$
Cell culture flask, Corning® cell culture flasks, surface area 75 $cm^2$, Cat.No: CLS430641-100EA, Sigma Aldrich
FINNTIP 300 µl (VWR, 613-2614)
Pipette tips 1000 µl FINNTIP, Cat. No: 613-4485, VWR
96-well V bottom plate (Nunc, Denmark)
Trypan Blue, Cat.No: T8154, batch no. RNBD3142, Sigma
Reagent reservoirs 100 ml, Cat. No: 89094-656, Lot: 96817, VWR
Safety Instructions
Saponin can cause eye and respiratory irritation, and inflammation of the skin contact in some persons.
Wear gloves to avoid skin contact with saponin etc.
Work in hood to avoid inhalation of chloroform
Experimental Set Up
Prepare serial dilution of NanoQuil F70 particles to concentrations from 1000 µg/ml down to 0.32 µg/ml (1:5 dilutions) in PBS pH 7,4. The final concentration on cells will be from 100 µg/ml to 0.032 µg/ml on cells. Use PBS for blank cell control.

METHODS

Viability Test
Pour the U937-1 cells in culture medium into a falcon tube
Spin down the cells at 200 g for 5-10 minutes.
Pour out the cell culture medium.
Resuspend the cells in pre-warmed new medium.
Count the cells and determine the viability by Trypan blue staining (viability should be ≥90%).
Adjust cell concentration to $0.11 \times 10^6$ cells/ml
Seed the cells in 96-well micro-titre plates at a cell density of ~20 000 cells/well (180 µl).
Add NanoQuil F70 formulations to the wells (20 µl) (use PBS in control untreated cells)
Put the plate at 37° C. in humidified atmosphere containing 5% $CO_2$ during incubation time.
After 66 hour add 20 µl Alamar blue and measure the fluorescence (or absorbance) signal every hour for 6 hours (in total 72 hours) at 570 and 620 nm by spectrophotometry.
Results
The QS-21 fraction of quillaja saponin formulated into nano particles has previously been shown to induce apoptosis in several cancer cell lines, as described in WO2013051994 and WO2014163558. The apoptotic effect of NanoQuil F70 particles tested herein on the monocytic cell line U937-1 measured by Alamar blue assay shows an EC50 of between 0.15 and 0.25 mg/ml after 3 days of incubation.

The invention claimed is:
1. Nanoparticles comprising cholesterol and a quillaja saponin, wherein the ratio between the quillaja saponin and the cholesterol is from 12:1 to 18:1 and the nanoparticles are thread-like, have a filament diameter or thickness of between 4-8 nm, and comprise two forms:
   Form A, composed of closed, substantially circular nanoparticles with a radius of between 10-15 nm and
   Form B, composed of open-ended, worm-like nanoparticles with a length of 35-45 nm.
2. The nanoparticles according to claim 1, wherein the ratio of Form A to Form B in the mixture is from between 20:80 to 45:55.
3. The nanoparticles according to claim 1, wherein the ratio between quillaja saponin and cholesterol is from 14:1 to 17:1.
4. The nanoparticles according to claim 1, further comprising at least one amphipathic or hydrophobic molecule selected from an antigen, an adjuvant, a targeting molecule, a pharmaceutical compound and a food related compound.
5. A pharmaceutical composition comprising one or more nanoparticles according to claim 1.
6. The pharmaceutical composition according to claim 5, further comprising at least one pharmaceutically active compound, wherein the active compound may be integrated into the nanoparticle or mixed with the composition.
7. The nanoparticles according to claim 1, formulated as a pharmaceutical composition further comprising pharmaceutically acceptable buffers, diluents, excipients, adjuvants and/or carriers.
8. A method for producing nanoparticles according to claim 1, comprising:
   a. preparing a layer of cholesterol on the inner surface of a reaction vessel and/or on the surface of a water-insoluble, porous article located in the reaction vessel, by removing the solvent from a non-aqueous solution of cholesterol in an organic solvent selected from one or more $C_1$-$C_6$ alcohols, $C_2$-$C_6$ ketones, $C_1$-$C_6$ alkyl esters of $C_1$-$C_3$ carboxylic acids, and linear or cyclic $C_4$-$C_8$ ethers,
   b. adding an aqueous reaction medium, which may be a solution of one or more salts, a buffer solution, or salt-free distilled water, c. adding a solution of triterpenoid saponins to a final concentration of 1 mg/ml to 10 mg/mL to produce a final ratio of 12:1 to 18:1 (w/w) saponin: cholesterol, d. heating the reaction mixture at 70° C.±5° C. for about an hour, e. cooling the reaction mixture to 4° C.±2° C. overnight, isolating the formed particles and removing excess saponin.

9. The method according to claim 8, wherein the organic solvent is ethanol and/or acetone.

10. The method according to claim 8, wherein the organic solvent is removed by evaporation.

11. The method according to claim 8, wherein the aqueous reaction medium is an acetate buffer.

12. The method according to claim 8, wherein the aqueous reaction medium is PBS buffer.

13. The method according to claim 8, wherein the removal of excess saponin is performed by size exclusion chromatography (SEC) on a suitable gel filtration medium.

* * * * *

UNITED STATES PATENT AND TRADEMARK OFFICE
CERTIFICATE OF CORRECTION

Page 1 of 1

PATENT NO. : 12,268,740 B2
APPLICATION NO. : 17/312796
DATED : April 8, 2025
INVENTOR(S) : Kefei Hu, Laurent Duroux and Erik Lindblad It is certified that error appears in the above-identified patent and that said Letters Patent is hereby corrected as shown below:

In the Specification

In Column 1 after Line 2 and below "VACCINE ADJUVANT EFFECT": insert -- This application is a U.S. National Phase application of PCT International Application No. PCT/EP2019/085444, filed December 16, 2019, which claims the benefit of EP 18213540.0, filed December 18, 2018, both of which are incorporated by reference herein in their entireties. --

Signed and Sealed this
First Day of July, 2025

Coke Morgan Stewart
*Acting Director of the United States Patent and Trademark Office*